US009062127B2

(12) United States Patent
Voss et al.

(10) Patent No.: US 9,062,127 B2
(45) Date of Patent: *Jun. 23, 2015

(54) METHOD FOR RATIONAL MUTAGENESIS OF α/βT-CELL RECEPTORS AND CORRESPONDINGLY MUTATED MDM2-PROTEIN SPECIFIC α/βT-CELL RECEPTORS

(75) Inventors: Ralf-Holger Voss, Ingelheim (DE); Theobald Matthias, Mainz (DE)

(73) Assignee: JOHANNES GUTENBERG-UNIVERSITAT MAINZ, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,259

(22) Filed: Nov. 23, 2010

(65) Prior Publication Data

US 2011/0243995 A1 Oct. 6, 2011

Related U.S. Application Data

(63) Continuation of application No. 10/529,072, filed as application No. PCT/EP03/10633 on Sep. 24, 2003, now Pat. No. 7,871,817.

(30) Foreign Application Priority Data

Sep. 24, 2002 (DE) .................................. 10244457

(51) Int. Cl.

| *C12N 15/63* | (2006.01) |
|---|---|
| *C07H 21/04* | (2006.01) |
| *C07K 1/00* | (2006.01) |
| *C07K 14/00* | (2006.01) |
| *C07K 14/725* | (2006.01) |
| *C07K 14/435* | (2006.01) |

(52) U.S. Cl.
CPC ............. *C07K 14/7051* (2013.01); *C12N 15/63* (2013.01); *C07K 14/435* (2013.01); *C07H 21/04* (2013.01)

(58) Field of Classification Search
CPC ...... C12N 15/63; C07H 21/04; C07K 14/435; C07K 14/7051
USPC ........................... 435/455; 536/23.5; 530/350
See application file for complete search history.

(56) References Cited

U.S. PATENT DOCUMENTS

| 7,871,817 B2 * | 1/2011 | Voss et al. ...................... 435/455 |
|---|---|---|
| 2002/0064521 A1 | 5/2002 | Ellenhorn et al. |
| 2004/0171111 A1 | 9/2004 | Stanislawski et al. |

FOREIGN PATENT DOCUMENTS

| CA | 2445004 | 12/2002 |
|---|---|---|
| CA | 2445013 | 12/2002 |
| DE | 101 09 855 | 9/2002 |
| WO | WO 96/27011 | 9/1996 |
| WO | WO 99/16867 | 4/1999 |
| WO | WO 02/070552 | 9/2002 |

OTHER PUBLICATIONS

Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Backstrom, B. T. et al., "A Motif Within the T Cell Receptor Alpha Chain Constant Region Connecting Peptide Domain Controls Antigen Responsiveness," *Immunity*, 1996, 5(5):437-447.
Chang, H-C. et al., "A General Method for Facilitating Heterodimeric Pairing Between Two Proteins: Application to Expression of Alpha and Beta T-Cell Receptor Extracellular Segments," *Proceedings of the National Academy of Sciences of USA*, 1994, 91(24):11408-11412.
Li, Z. G. et al., "Structural Mutations in the Constant Region of the T-Cell Antigen Receptor (TCR) Beta Chain and Their Effect on TCR Alpha and Beta Chain Interaction," *Immunology*, 1996, 88(4):524-530.
Stanislawski, T. et al., "Circumventing Tolerance to a Human MDM2-Derived Tumor Antigen by TCR Gene Transfer," *Nature Immunology*, 2001, 2(10):962-970.
Garcia, K. C. et al. "An αβ T Cell Receptor Structure at 2.5 Å and its Orientation in the TCR-MHC Complex" *Science*, Oct. 11, 1996, pp. 209-219, vol. 274.
Ogris, M. et al. "Targeting tumors with non-viral gene delivery systems" *Drug Discovery Today*, Apr. 2002, pp. 479-485, vol. 7, No. 8.
Voss, R. et al. "Molecular Design of the Cαβ Interface Favors Specific Pairing of Introduced TCRαβ in Human T Cells" *Journal of Immunology*, 2008, pp. 391-401, vol. 180.
Kaye, F. J. et al. "A single amino acid substitution results in a retinoblastoma protein defective in phosphorylation and oncoprotein binding" *Proc. Natl. Acad. Sci. USA*, Sep. 1990, pp. 6922-6926, vol. 87.
Davis, C. G. "The Many Faces of Epidermal Growth Factor Repeats" *The New Biologist*, May 1990, pp. 410-419, vol. 2, No. 5.
Skolnick, J. et al. "From genes to protein structure and function: novel applications of computational approaches in the genomic era" *Trends in Biotech.*, Jan. 2000, pp. 34-39, vol. 18.
Deonarain, M. P. "Ligand-targeted receptor-mediated vectors for gene delivery" *Exp. Opin. Ther. Patents*, 1998, pp. 53-69, vol. 8, No. 1.
Eck et al., *Goodman & Gilman's The Pharmacological Basis of Therapeutics*, McGraw-Hill, New York, 1996, p. 77-101.
Verma, I. M. et al., "Gene therapy—promises, problems and prospects,"*Nature*, Sep. 1997, pp. 239-242, vol. 389.

(Continued)

*Primary Examiner* — Shin Lin Chen
(74) *Attorney, Agent, or Firm* — Saliwanchik, Lloyd & Eisenschenk

(57) ABSTRACT

The invention relates to the rational mutagenesis of polypeptides of α/β T-cell receptors that mediate an oncogen-specific T-cell response, nucleic acids encoding these and their use in the therapy, diagnosis and/or prevention of cancerous diseases. The invention further relates to a T-cell response-mediating MDM2-protein-specific α/β T-cell receptor, which has been rationally mutated by means of the method according to the present invention, and the uses thereof.

16 Claims, 13 Drawing Sheets

(56) References Cited

OTHER PUBLICATIONS

Gorecki, D. C. "Prospects and problems of gene therapy: an update" *Expert Opin. Emerging Drugs*, 2001, pp. 187-198, vol. 6, No. 2.

Thomas, C. E. et al., "Progress and Problems with the Use of Viral Vectors for Gene Therapy" *Nature*, May 2003, pp. 346-358, vol. 4.

Call, M. E. et al. "Common themes in the assembly and architecture of activating immune receptors", *Nature Reviews*, Nov. 2007, pp. 841-850, vol. 7.

Kuhns, M. S. et al. "Disruption of Extracellular Interactions Impairs T Cell Receptor-CD3 Complex Stability and Signaling" *Immunity*, Mar. 2007, pp. 357-369, vol. 26.

Kuhns, M. S. et al. "Deconstructing the Form and Function of the TCR/CD3 Complex" *Immunity*, pp. 133-139, vol. 24, 2006.

Call, M. E. et al. "Molecular mechanisms for the assembly of the T cell receptor-CD3 complex" *Molecular Immunology*, 2005, pp. 1295-1305, vol. 40.

Raper, S. E. "Gene Therapy: The good, the bad, and the ugly" *Surgery*, May 2005, pp. 487-492, vol. 137, No. 5.

Lefranc, M.-P. "IMGT, the international ImMunoGeneTics database" *Nucleic Acids Research*, 2001, pp. 207-209, vol. 29. No. 1.

Kuball, J. et al. "Facilitating matched pairing and expression of TCR chains introduced into human T cells" *Blood*, 2007, pp. 2331-2338, vol. 109.

Van Loenen, M. M. et al. "Mixed T cell receptor dimers harbor potentially harmful neoreativity" *Proceedings of the National Academy of Sciences*, Jun. 15, 2010, pp. 10972-10977, vol. 107, No. 24.

Call, M. E. et al. "The Organizing Principle in the Formation of the T Cell Receptor-CD3 Complex" *Cell*, Dec. 27, 2002, pp. 967-979, vol. 111.

\* cited by examiner

Figure 2:
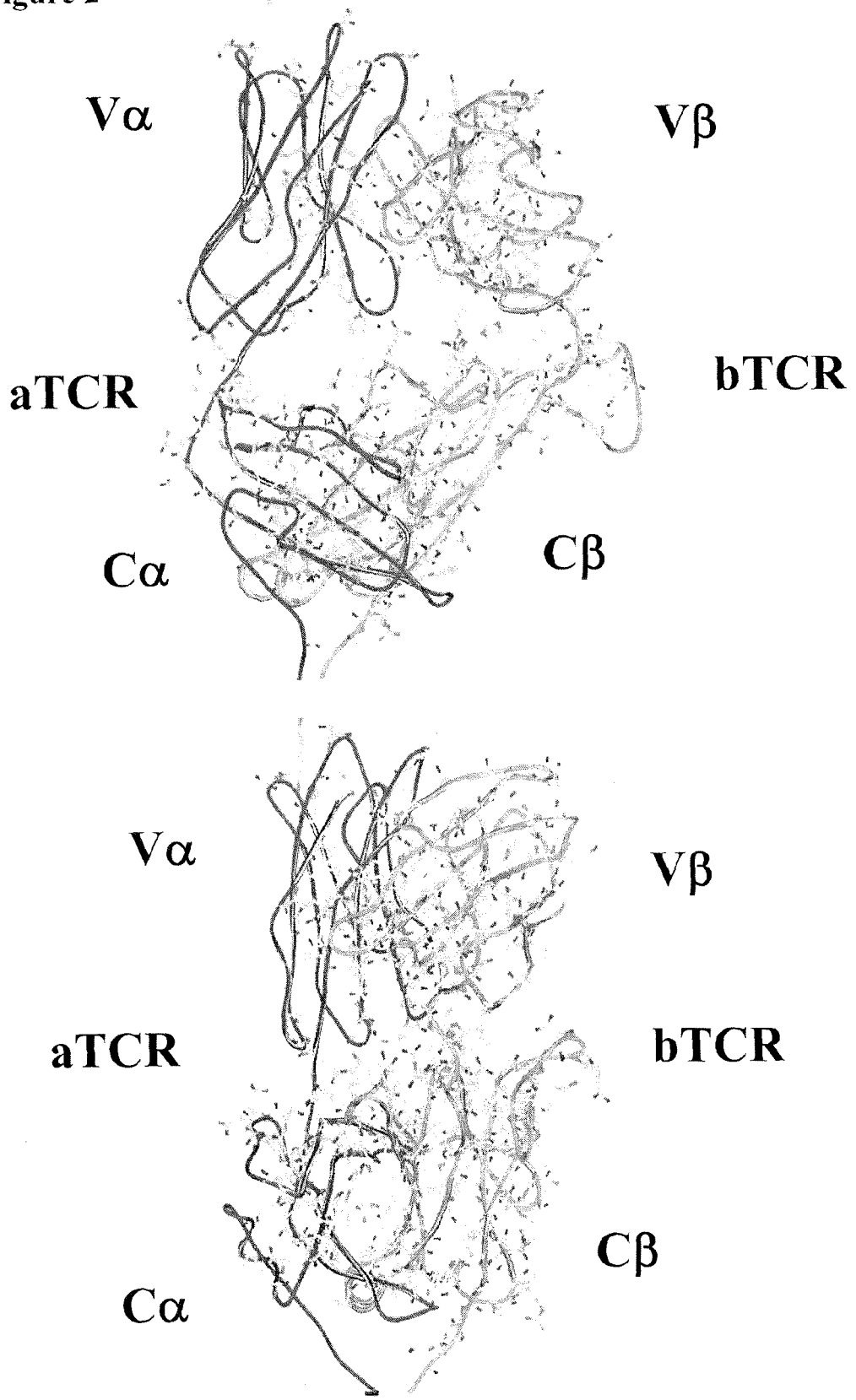

Figure 2  Identical amino acids 1tcr.pdb / 1bd2.pdb

Figure 4A:
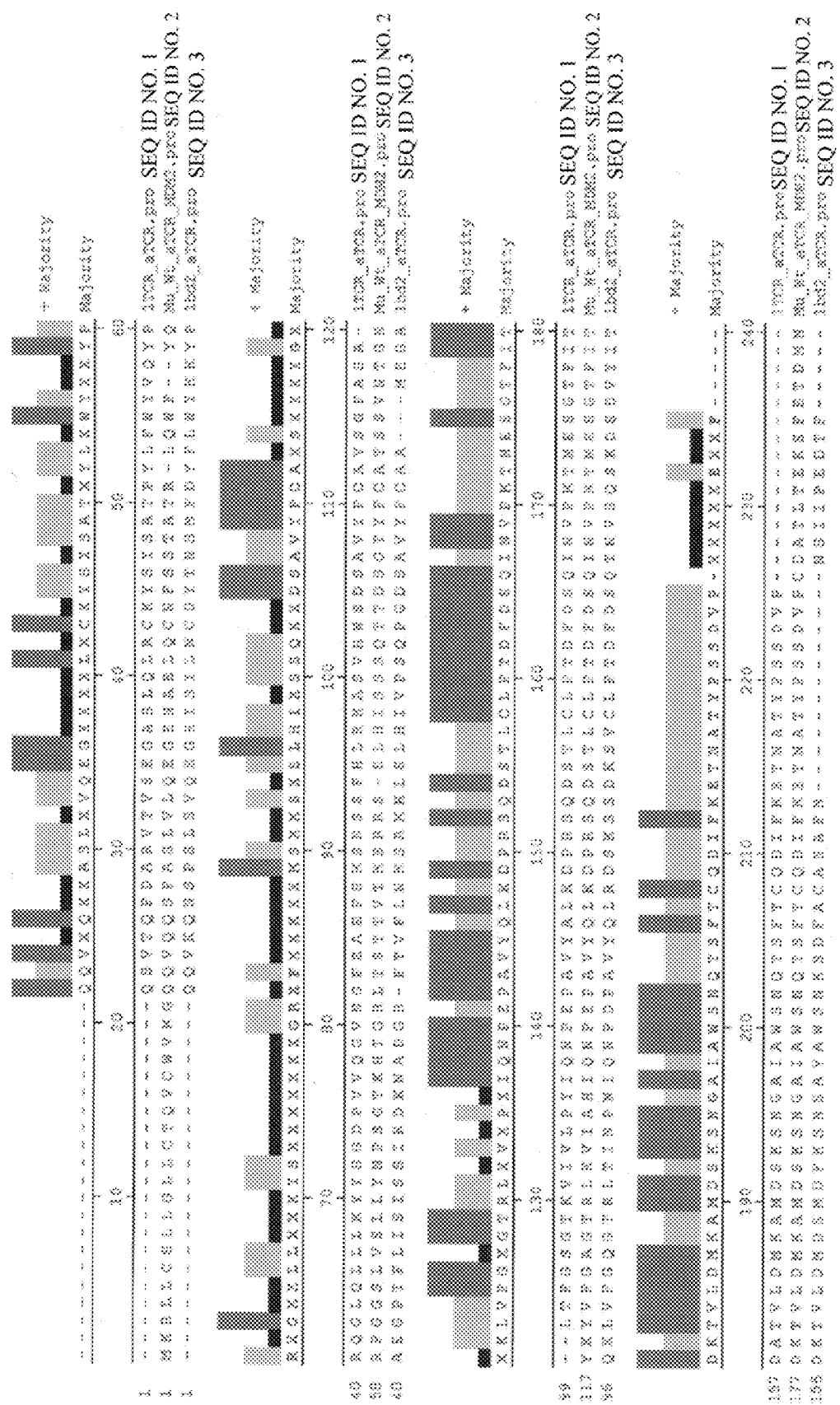
Figure 4B:
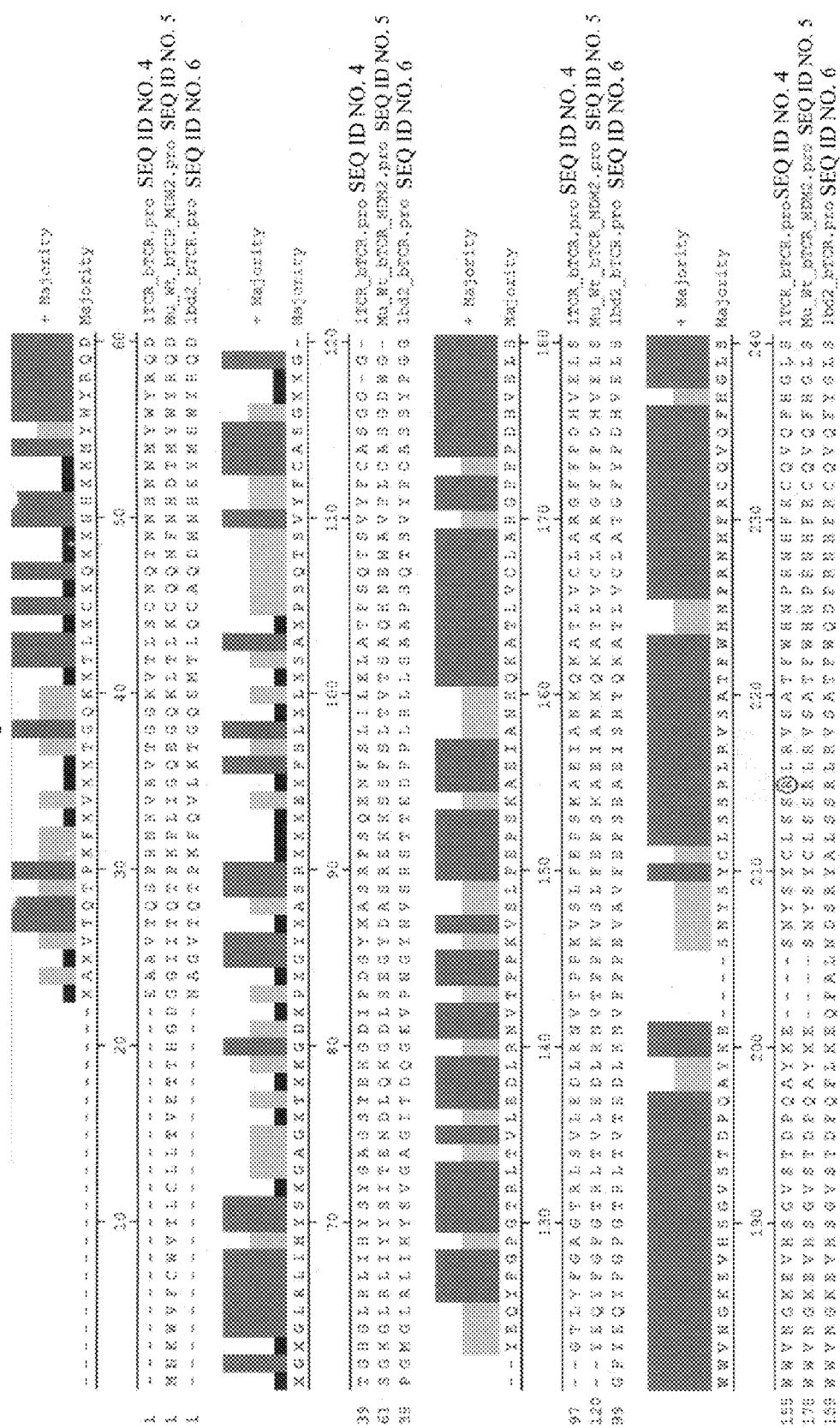

Figure 4b (continued)

1tcr.pdb

SEQUENCE LISTING

```
<160> NUMBER OF SEQ ID NOS: 6

<210> SEQ ID NO 1
<211> LENGTH: 200
<212> TYPE: PRT
<213> ORGANISM: Mus musculus

<400> SEQUENCE: 1

Gln Ser Val Thr Gln Pro Asp Ala Arg Val Thr Val Ser Glu Gly Ala
1               5                   10                  15

Ser Leu Gln Leu Arg Cys Lys Tyr Ser Tyr Ser Ala Thr Pro Tyr Leu
            20                  25                  30

Phe Trp Tyr Val Gln Tyr Pro Gln Gly Leu Gln Leu Leu Leu Lys Tyr
        35                  40                  45

Tyr Ser Gly Asp Pro Val Val Gln Gly Val Asn Gly Phe Glu Ala Glu
    50                  55                  60

Phe Ser Lys Ser Asn Ser Ser Phe His Leu Arg Lys Ala Ser Val His
65                  70                  75                  80

Trp Ser Asp Ser Ala Val Tyr Phe Cys Ala Val Ser Gly Phe Ala Ser
                85                  90                  95

Ala Leu Thr Phe Gly Ser Gly Thr Lys Val Ile Val Leu Pro Tyr Ile
            100                 105                 110
```

Gln Asn Pro Glu Pro Ala Val Tyr Ala Leu Lys Asp Pro Arg Ser Gln
            115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Ala Thr Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro
            195                 200

<210> SEQ ID NO 2
<211> LENGTH: 236
<212> TYPE: PRT
<213> ORGANISM: Mus musculus

<400> SEQUENCE: 2

Met Lys Arg Leu Leu Cys Ser Leu Leu Gly Leu Leu Cys Thr Gln Val
1               5                   10                  15

Cys Trp Val Lys Gly Gln Gln Val Gln Gln Ser Pro Ala Ser Leu Val
            20                  25                  30

Leu Gln Glu Gly Glu Asn Ala Glu Leu Gln Cys Asn Phe Ser Ser Thr
        35                  40                  45

Ala Thr Arg Leu Gln Trp Phe Tyr Gln Arg Pro Gly Gly Ser Leu Val
    50                  55                  60

Ser Leu Leu Tyr Asn Pro Ser Gly Thr Lys His Thr Gly Arg Leu Thr
65                  70                  75                  80

Ser Thr Thr Val Thr Lys Glu Arg Arg Ser Ser Leu His Ile Ser Ser
                85                  90                  95

Ser Gln Thr Thr Asp Ser Gly Thr Tyr Phe Cys Ala Thr Ser Ser Val
            100                 105                 110

Asn Thr Gly Asn Tyr Lys Tyr Val Phe Gly Ala Gly Thr Arg Leu Lys
        115                 120                 125

Val Ile Ala His Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn
225                 230                 235

<210> SEQ ID NO 3
<211> LENGTH: 196
<212> TYPE: PRT
<213> ORGANISM: Homo sapiens

<400> SEQUENCE: 3

```
Gln Gln Val Lys Gln Asn Ser Pro Ser Leu Ser Val Gln Glu Gly Arg
1               5                   10                  15

Ile Ser Ile Leu Asn Cys Asp Tyr Thr Asn Ser Met Phe Asp Tyr Phe
            20                  25                  30

Leu Trp Tyr Lys Lys Tyr Pro Ala Glu Gly Pro Thr Phe Leu Ile Ser
                35                  40                  45

Ile Ser Ser Ile Lys Asp Lys Asn Ala Asp Gly Arg Phe Thr Val Phe
50                  55                  60

Leu Asn Lys Ser Ala Lys His Leu Ser Leu His Ile Val Pro Ser Gln
65                  70                  75                  80

Pro Gly Asp Ser Ala Val Tyr Phe Cys Ala Ala Met Glu Gly Ala Gln
                85                  90                  95

Lys Leu Val Phe Gly Gln Gly Thr Arg Leu Thr Ile Asn Pro Asn Ile
                100                 105                 110

Gln Asn Pro Asp Pro Ala Val Tyr Gln Leu Arg Asp Ser Lys Ser Ser
            115                 120                 125

Asp Lys Ser Val Cys Leu Phe Thr Asp Phe Asp Ser Gln Thr Asn Val
            130                 135                 140

Ser Gln Ser Lys Asp Ser Asp Val Tyr Ile Thr Lys Thr Val Leu Asp
145                 150                 155                 160

Met Asp Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe
            195

<210> SEQ ID NO 4
<211> LENGTH: 236
<212> TYPE: PRT
<213> ORGANISM: Mus musculus

<400> SEQUENCE: 4

Glu Ala Ala Val Thr Gln Ser Pro Arg Asn Lys Val Ala Val Thr Gly
1               5                   10                  15

Gly Lys Val Thr Leu Ser Cys Asn Gln Thr Asn Asn His Asn Asn Met
            20                  25                  30

Tyr Trp Tyr Arg Gln Asp Thr Gly His Gly Leu Arg Leu Ile His Tyr
                35                  40                  45

Ser Tyr Gly Ala Gly Ser Thr Glu Lys Gly Asp Ile Pro Asp Gly Tyr
50                  55                  60

Lys Ala Ser Arg Pro Ser Gln Glu Asn Phe Ser Leu Ile Leu Glu Leu
65                  70                  75                  80

Ala Thr Pro Ser Gln Thr Ser Val Tyr Phe Cys Ala Ser Gly Gly Gly
                85                  90                  95

Gly Thr Leu Tyr Phe Gly Ala Gly Thr Arg Leu Ser Val Leu Glu Asp
                100                 105                 110

Leu Arg Asn Val Thr Pro Pro Lys Val Ser Leu Phe Glu Pro Ser Lys
            115                 120                 125

Ala Glu Ile Ala Asn Lys Gln Lys Ala Thr Leu Val Cys Leu Ala Arg
            130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Ala Tyr Lys Glu Ser
                165                 170                 175
```

Asn Tyr Ser Tyr Cys Leu Ser Ser Arg Leu Arg Val Ser Ala Thr Phe
            180                 185                 190

Trp His Asn Pro Arg Asn His Phe Arg Cys Gln Val Gln Phe His Gly
        195                 200                 205

Leu Ser Glu Glu Asp Lys Trp Pro Glu Gly Ser Pro Lys Pro Val Thr
210                 215                 220

Gln Asn Ile Ser Ala Glu Ala Trp Gly Arg Ala Asp
225                 230                 235

<210> SEQ ID NO 5
<211> LENGTH: 307
<212> TYPE: PRT
<213> ORGANISM: Mus musculus

<400> SEQUENCE: 5

Leu Met Asn Lys Trp Val Phe Cys Trp Val Thr Leu Cys Leu Leu Thr
1               5                   10                  15

Val Glu Thr Thr His Gly Asp Gly Gly Ile Ile Thr Gln Thr Pro Lys
            20                  25                  30

Phe Leu Ile Gly Gln Glu Gly Gln Lys Leu Thr Leu Lys Cys Gln Gln
        35                  40                  45

Asn Phe Asn His Asp Thr Met Tyr Trp Tyr Arg Gln Asp Ser Gly Lys
    50                  55                  60

Gly Leu Arg Leu Ile Tyr Tyr Ser Ile Thr Glu Asn Asp Leu Gln Lys
65                  70                  75                  80

Gly Asp Leu Ser Glu Gly Tyr Asp Ala Ser Arg Glu Lys Lys Ser Ser
                85                  90                  95

Phe Ser Leu Thr Val Thr Ser Ala Gln Lys Asn Glu Met Ala Val Phe
            100                 105                 110

Leu Cys Ala Ser Gly Asp Trp Gly Tyr Glu Gln Tyr Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser

-continued

```
305

<210> SEQ ID NO 6
<211> LENGTH: 244
<212> TYPE: PRT
<213> ORGANISM: Homo sapiens

<400> SEQUENCE: 6

Asn Ala Gly Val Thr Gln Thr Pro Lys Phe Gln Val Leu Lys Thr Gly
1               5                  10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Pro
                85                  90                  95

Gly Gly Gly Phe Tyr Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp
```

METHOD FOR RATIONAL MUTAGENESIS OF α/βT-CELL RECEPTORS AND CORRESPONDINGLY MUTATED MDM2-PROTEIN SPECIFIC α/βT-CELL RECEPTORS

CROSS-REFERENCES TO RELATED APPLICATIONS

This application is a continuation of U.S. Ser. No. 10/529,072, filed Oct. 14, 2005, now U.S. Pat. No. 7,781,817, which is the national stage application of International Application Number PCT/EP2003/010633, filed Sep. 24, 2003, the disclosures of which are hereby incorporated by reference in their entireties, including all figures, tables and amino acid or nucleic acid sequences.

The invention relates to the rational mutagenesis of polypeptides of α/β T-cell receptors that mediate an oncogen-specific T-cell response, nucleic acids encoding these and their use in the therapy, diagnosis and/or prevention of cancerous diseases. The invention further relates to a T-cell response-mediating MDM2-protein-specific α/β T-cell receptor, which has been rationally mutated by means of the method according to the present invention, and its uses.

The antigen recognition by T-lymphocytes (TLC) is critical for the generation and regulation of an effective immune response. The characteristic T-cell line-marker is the T-cell-antigen-receptor (TCR). There are two types of TCR differentiated by sequence: the heterodimeric α/β-TCR, and the structurally related γ/δ-TCR. The respective pairs of chains are covalently linked by a disulfide bridge, and are associated with a set of five polypeptides, the CD3-complex, and together form the T-cell receptor-complex (TCR-CD3-complex). The α/β-TCR is the functionally most relevant, since it is expressed in more than 95% of all T-cells, and mediates the primary immune response.

α/β-T-Cells can be separated in two different overlapping populations: One subgroup, which carries the CD4-marker and mainly supports the immune response ($T_H$), and a subgroup which carries the CD8-marker and is essentially cytotoxic ($T_C$). $CD8^+$-T-cells recognize antigens in association with MHC-class-I-molecules. Such antigens, amongst others, can be tumor-specific or tumor-associated peptide antigens. Following recognition of the peptide antigens, the respective cell is killed in that the T-cell lyses the target cell and/or induces apoptosis of these target cells or releases cytokines (e.g. IL-2, IFN-γ). This constitutes an essential functional difference, compared to antibodies: TCR exclusively recognize peptide antigens in the context of the MHC-presentation, whereas antibodies recognize sequential or conformational peptide antigens independently from further accessory molecules. Thus, TCRs are the suitable molecular tools in order to recognize tumor protein-derived antigens, and for coupling them directly to a cytotoxic T-cell-response. In turn, antibodies primarily have the function of recognizing surface markers of cells as pathogenic, and to label them in order to be eliminated in the following by other effector cells, e.g. macrophages, via phagocytosis.

Among the tumor associated peptide antigens (TAA) that are presented in the context of MHC-class-1-molecules on the surface of tumor cells, the so-called "universal" TAA are of particular interest. These TAA are mainly derived from cellular proteins that are weakly expressed in normal cells and over-expressed in tumor cells. Belonging to these proteins, amongst others, is the human homolog of the "mouse-double-minute-2" proto-oncogene (mdm2), the so-called "human mdm2" or, abbreviated, "MDM2" proto-oncoprotein (Roth et al. 1998), that is not only over-expressed in a variety of solid tumors but also in hematological neoplasia (malign hematological systemic diseases), AML, ALL and CLL (Zhou et al, 2000).

Oligopeptides of the MDM2-protein can be presented in the context with MHC-class-1-molecules on the cellular surface, and represent attractive target structures for CD8-positive T-cells. Here, the extent of the course of the T-cell response stays within a defined kinetic window (Kersh et al., 1998). The complex of peptide-MHC and TCR-CD3 multimerises in order to effect an efficient signal transduction, in which the exact stoichiometry and the extent of the oligomerisation is still controversial.

The present invention relates to a biochemical problem in the area of applied immunology & oncology: Focus of the invention is the development of highly-effective T-cells that are able to specifically recognize and lyse human (Hu) tumor cells via their cytotoxic effector-function. For this, CTL-clones which recognize specific TAA are isolated in a transgenic murine (Mu) or mouse-model (Stanislawski & Voss et al., 2001). Responsible for the oncoprotein derived peptide-recognition on the side of the T-cells is the membrane stemming TCR that recognizes the complex out of membrane stemming MHC-molecule and presented peptide, which, on the side of the antigen presenting cell (APC) or also tumor cell, has arisen from the proteosomal processing of oncoproteins, and mediates an activating signal to the signal transduction cascade of the cytotoxic T-cell (CTL).

The prospective clinical use envisages isolating peripheric T-cells from the blood of a tumor patient, adding the gene of the TAA-specific TCR by adoptive gene technology based transfer, and, following massive expansion, re-infusing (Rosenberg, 1999; Schumacher, 2002).

The T-cell-receptor is a heterodimeric α/β-molecule, whose chains are each uniquely spanning the transmembrane. Each chain consists out of two globular domains that have an immunoglobulin-like folding: the amino terminal domain is designated as the variable domain (Vα or Vβ, respectively), since it is derived from genetic rearrangement, and is responsible for the individual peptide recognition. The domain that follows is called the invariant or also constant domain (Cα or Cβ, respectively), since it is highly conserved, and essentially has a spacer function for the variable domain to the cellular membrane, as well as regulatory proteins that bind to it. Finally, the section of a transmembrane region and a short carboxy terminal cytoplasmatic end, whereto the signal transducing CD3-complex is able to bind, do follow. This arrangement is valid to the same extent for human and for murine TCR: the foreign-species protein-backbone is superimposable with only a marginal difference of merely 1.04 Angstrom. In particular in the constant domain numerous amino acids are homologous or identical, respectively (see FIG. 1), as exemplary shown for a murine (1) compared to a human, HLA-A2.1-restringed TCR (1bd2). Although the T-cell-receptor is a heterodimer molecule made from two polypeptide-chains, in contrast to the antibody it has a monovalent binding site. Antibodies in principle are homodimers of heterodimeric subunits, from which a bivalent antigen recognition of one and the same antibody results (i.e. monospecific): two identical arms, each consisting of a heterodimeric attachment of a heavy and a light chain, which therefore form an antigen-binding site, are covalently connected via a disulfide bridge. From this, contact areas result between the arms of an antibody that are not present in a TCR: this generated the object (Atwell et al., 1997; WO 96/27011) to modify the bivalent antigen recognition in such a way to let each of both antigen-binding sites recognize a different antigen, i.e. to introduce a bispecificity into the complete antibody molecule. Finally, this exemplary provides a basis for an antibody that recognizes a tissue specific antigen as well as a pathogenic antigen. This goal can not be realized in a TCR, since it structurally corresponds only to one of both arms of an antibody, and is also monovalent, and therefore mandatory monospecific.

A different object results for the therapeutic use of TCRs: in that the polyclonal T-cell population of the patient carries individual so-called endogenic T-cell-receptors of unknown specificity. A functional TCR is formed out of the pairing of both chains via the endoplasmatic reticulum (ER)- and Golgi-processing pathway into a TCR/CD3-complex which is directed to the cellular surface. Since the heterodimeric chains are first expressed separately and, in addition, a sufficient homology between the human and murine chains exists, the exogenically added TCR are able to pair with the endogenic chains, and elicit unknown, in the worst case unwanted, monospecificities (autoimmune reactions). In the simplest case, the four chains as present (two endogenic and two exogenic chains) in a T-cell being transduced with the genes for a TCR result into four conceivable combinations, out of which two are unwanted Hu α/Mu β and Mu α/Hu β-hybrids. Further, the situation gets more complicated, if several TCR-genes specific for different TAAs are transduced, or due to the fact that in some instances in one T-cell, due to an insufficient allelic exclusion of one of the two genomic α-chains, two functional TCRs are expressed. Furthermore, in the context of a clinical application, presumably non-clonal T-cell-populations will be transduced, such that out of this a multitude of conceivable hybrid TCR are present on the population level.

Such a hybrid form has not yet been shown, nevertheless, based on the structural data, such as TCR-protein crystal structures present so far (Garcia et al., 1998; Ding et al., 1998), it can not be excluded. Nevertheless, it could be shown in the laboratory of the inventors that a foreign single mouse-TCRβ-chain that is introduced into human T-cells is only expressed on the surface if it is able to pair with the endogenic human TCRα-chains. Since this could be shown, and the exogenic expression was amplifiable in case of partially humanized β-chains or was diminishable through the introduction of point mutations that interfere with the pairing (see approach "compensated introduction of an exposed carrier of charge" described below), this is a strong indication towards the presence of hybrid TCRs. It is therefore mandatory for an increased safety in the use of TCR to exclude such hybrid forms as much as possible.

One resolving way for an avoidance of the unwanted pairing of chains is the design of single chain T-cell receptors. This approach was initially developed for antibodies (Eshhar et al., 1993; 2001), but could be transferred to the latter based on the structural homologies between antibodies and T-cell receptors (Chung et al., 1994; Weijtens et al., 1998; Willemsen et al., 2000). For this, the variable domains are covalently linked one with the other via a short peptide, a "linker", omitting one of the two constant domains. Such constructs can be freely designed by genetic engineering and guarantee for a biochemically coupled 1:1-stoichiometry of the heterodimeric variable domains (for this, see also FIG. 3).

Alternatively, short peptide sequences are genetically attached to the respective chains of the heterodimeric molecule that function as affinity-tags that provide for a specific pairing of chains: for this, carboxy-terminal "tags" of 30 amino acids in length, so-called "leucine zipper", were added to T-cell receptors as a dimerisation motif (Chang et al., 1994). The latter methods have the drawback that they due to their recombinant character represent potential foreign antigens which lead to rejecting reactions in the acceptor organism.

In addition, the modified primary- and tertiary structure being markedly different from the wild type structure of human as well as murine TCR impede the stability and functionality of these chimeric constructs.

It is therefore the object of the present invention to provide a method that allows for a production of recombinant TCRs in such a way that preferably the externally introduced TCR-chains are pairing, and do not form mixed pairs with the endogenic chains of the T-cell, without at the same time affecting their functionality and stability.

Figure 11:
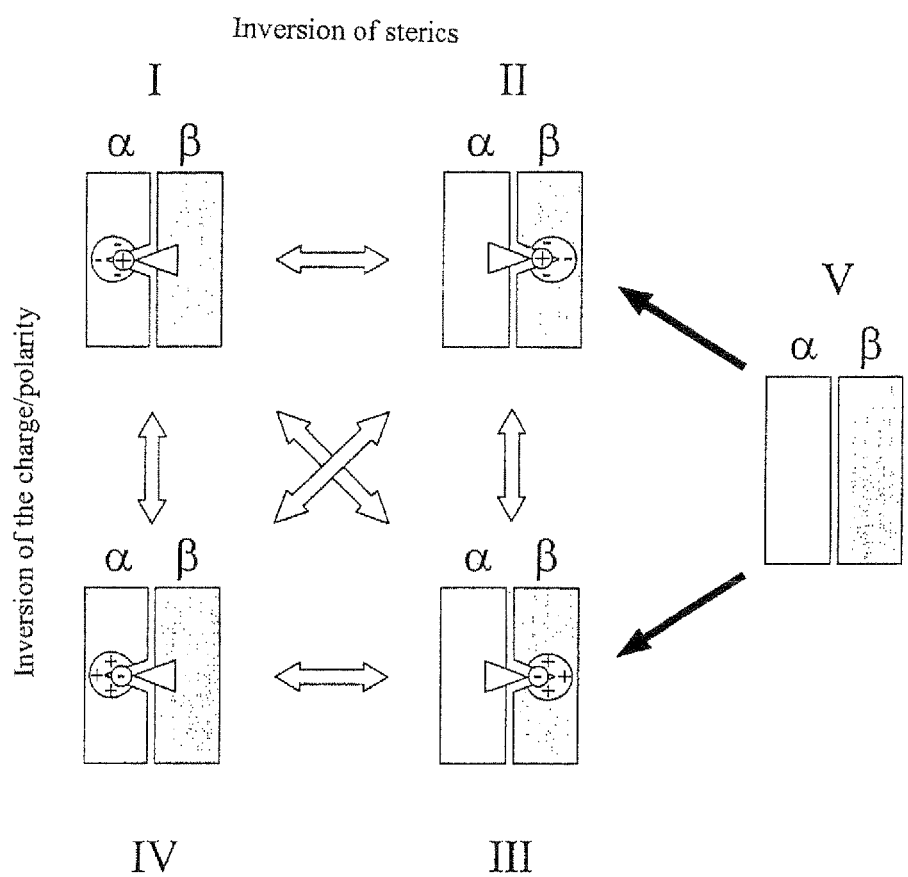

According to the invention, this object is solved by a method for producing a heterodimeric specific wild type- or chimeric T-cell receptor (TCR) containing a first chain and a second chain that interact one with another at least at one surface, wherein the at least one surface is subjected to a rational mutagenesis, such that the at least one surface of the first chain or the surface of the second chain comprises a sterically projecting group, that interacts with a sterically recessed group on the at least one surface of the corresponding first chain or second chain. Preferably, the sterically projecting group that is comprised by the at least one surface of the first chain or the surface of the second chain is a charged and/or polar group, and further preferred, the sterically recessing group on the at least one surface of the corresponding first chain or second chain is an opposingly charged and/or polar group. Here, it can be sufficient to introduce an exposed charge on one side, if the opposing contact area can cooperatively compensate for this modification, or it can be required to complementary introduce an opposing recessed charge. In the following, this novel approach with TCR shall be designated and described as the "compensated introduction of an exposed carrier of charge" (FIG. 11). Each "+"—but also "−"—symbol indicates a true charge or a polar charge. A true charge (e.g. the charged guanidium-group of arginine) can only be sufficiently compensated by several polar groups (e.g. carbonyles of the peptide groups) of several surfaces (amino acids). This is depicted by the non-stoichiometric illustration of the charge symbols: in many cases a sterically exposed true charge of the one chain (defined as sterically projecting group) projects into a recess of the cavity of the other chain (defined as sterically recessed group), which is lined with several polar or also charged groups. Even true charges are not directly compensated 1:1, since this also depends from the respective (dielectric) availability and distance of neighboring opposing charges. In view of the sterics as well as the charge, the respective groups need not to be directly converted 1:1, but this requires an individual structural analysis, optionally, e.g. by omission of a polar group within the cavity containing the charge carrier, in order to achieve an as much as possible compensatory effect. Not only the state V, wherein a respective inversely related charge carrier-surface is missing on the respective chains, corresponds to the wild type, but each of the states I-IV can also correspond to the initial status of the polypeptide chains as found.

Here, the possibility exists to exclusively invert the given steric relations (I/II or III/IV in FIG. 11, respectively), to invert the charges (I/IV or II/III in FIG. 11, respectively) or both (II/IV or I/III in FIG. 11, respectively). The particular case of an inversion of the charged and/or polar sterics (I/II of the FIG. 11) functions as example being experimentally shown on T-cell receptors (FIG. 2).

The method according to the invention comprises the steps of (a) providing the DNA-molecules, comprising the coding regions for the at least one surface to be mutated of the first chain or second chain in a joint or separate mutagenesis-vector system(s), (b) mutagenesis of the DNA-molecules in a manner known as such, wherein the nucleic acid sequence encoding for the at least one surface is modified compared to the initial sequence in such a way that, in the at least one surface of the first chain or the at least one surface of the second chain, a sterically projecting group, preferably charged and/or polar group is introduced, and in the corresponding interacting at least one surface of the second chain or the first chain, a sterically recessed group, preferably reversely charged and/or polar group, can be introduced, whereby individual mutated fragments are produced, c) translation of at least two of the individual mutated fragments from step b), such that the pairing of the heterodimeric specific first-chain/second-chain TCR being mutated at least one surface is selectively promoted, and d) presentation of the heterodimeric first-chain/second-chain TCR by a T-cell.

In the context of the present invention by a "surface" the area of a chain of a TCR shall be understood which interacts with a particular area of the second chain of the TCR. This interaction, either alone or in connection with others, leads to the formation of pairs of chains which form the active TCR. The sum of the interactions is based on electrostatic, dipole-dipole-, Van der Waals-contacts, and hydrophobic interactions that are determined by the amino acid sequences, as well as the structural positioning of the polypeptide chains amongst each other and to each other. In case of a punctual change, the secondary-, tertiary- and quaternary structure of the heterodimer should be unmodified. Without wanting to be bound to a particular mechanism of action, the inventors are assuming that generally the method of the present invention is aiming at influencing the combination of charge and sterics of side chain(s) without modifying the protein backbone. The modification of steric situations between interacting surfaces is insufficient in many cases, since even sterically large side chains (valine, phenylalanine) do modify the local structure by replacement of neighboring side chains, whether in relation to the own chain (surface) or the complementary chain (surface), in such a way that these are sterically accommodated within the contact area, without an effect on the pairing of the chains (surfaces). An effective contribution is performed by the rejection based on charge differences, since punctual charges, according to the law of Coulomb, function spherically in space with $1/Dr^2$. The affecting force exponentially decreases with an increasing distance and thus provides for a locally restricted effect of the punctual charge, without a far-reaching effect on the tertiary and quaternary structures. The dielectric constant D is lower in apolar milieus, as is the case in the inside of proteins or also at contact areas of subunits, and therefore the force that is acting on opposing charges is stronger. In order to amplify the effect on the surface interactions that is potentially induced (or is missing) by steric rejection (or even to initiate it), amino acid residues are chosen that have sterically exposed side chains with charges (e.g. arginine, lysine, glutamate), pH-inducible charges (e.g. histidine) or polar groups (e.g. glutamine). Preferably, this takes place by a modification on the level of the primary structure of the chain, that is is by amino acid exchanges inside the same. The punctual effect of the sterics as well as the charges of the two interacting surfaces (e.g. two interacting amino acids of opposing charge and reciprocal sterics) guarantee self-integrity of the sterical structures of the affected chains, but, nevertheless, in case of the interaction of two exposed or recessed identically charged surfaces, as would be the case for the interaction of an unmodified with a mutated chain, by the sterically limited distortion, induces a weakening of the pairing, whereas the complementary surfaces are neutralizing each other with respect to sterics and charge.

An alternative of the method according to the invention relates to a method, wherein the above-mentioned step c) above is replaced by the following steps: (c'), optionally, sub-cloning of the mutated fragments into suitable transfection-vector systems or virus-derived transduction systems, (c'') transfection or co-transfection or transduction of at least two of the mutated fragments into a mutant TCR-deficient T-cell, and (c''') expression of the heterodimeric first-chain/second-chain TCR in a recombinant T-cell. This alternative relates to the transfer of the genetic construct and its subsequent expression directly into a recombinant T-cell. Whilst this alternative is preferred, in an additional alternative of the method according to the invention, step c) above can be replaced by the following steps: c') In vitro-translation or in vivo-translation of at least two of the individual mutant fragments from step b) and, optionally, subsequent isolation and/or purification of the translated mutant fragments, such that the pairing of the heterodimeric specific first-chain/second-chain TCR being mutated on at least one surface is selectively promoted, and c'') introduction of the mutated specific first-chain/second-chain TCR into a T-cell.

For this, an expression of the mutated TCR occurs outside of the finally anticipated presenting T-cell, and a subsequent introduction of the TCR into the same. In case of the in vitro translation, the translation can occur in cell-free systems which are commercially available. The "translation", nevertheless, also comprises the purely synthetic production of the peptide chains as is explained in more detail further below in connection with the peptides. In case of the in vivo translation, this can take place in a suitable host cell that has been transformed with an expression construct of the chain in advance, and subsequently produces it. Suitable vectors and methods for expression are sufficiently known to the person of skill in the art. Following the expression, it can be required to either purify the expression products from the cells or to extract them from the medium, into which they have optionally been excreted by the host cell. Suitable host cells are also known and can be yeast, CHO-cells, insect cells, bacteria or other.

The introduction into the T-target cells can take place using any known manner that allows for a subsequent presentation of the TCR by the T-cell. Strategies are, for example, by means of the induction of phagocytosis by the cells or a method wherein the introduction occurs by lipid-mediated transfer, such as via micelles or liposome transfer. An overview about the use of liposomes, amongst others, is provided by the article of Banerjee R. Liposomes: applications in medicine. J Biomater Appl 2001 July; 16(1):3-21. The transfer via micelles is known to the person of skill in the art from numerous publications.

Preferably, according to the invention, as heterodimeric specific wild type or chimeric T-cell receptor (TCR), an alpha/beta TCR, gamma/delta TCR, a humanized or partially humanized TCR, a TCR being provided with additional (functional) domains, a TCR being provided with alternative domains, e.g., a TCR being provided with a different transmembrane domain as membrane anchor, is modified.

Backstrom et al. (Backstrom B T, Hausmann B T, Palmer E. Signaling efficiency of the T cell receptor controlled by a single amino acid in the beta chain constant region. J Exp Med. 1997 Dec. 1; 186(11):1933-8) describe a $Gln_{136}Phe$-mutation in the beta-TCR. The mutation is localized in the "beta chain connecting peptide domain", next to the transmembrane. The exchange as described is positioned far away from the point mutations that have been determined as useable for the rational mutagenesis by the present invention. In addition, an effect on the pairing of the chains is not analyzed, but exclusively a functionality of the TCR.

Backstrom et al. (Backstrom B T, Milia E, Peter A, Jaureguiberry B, Baldari C T, Palmer E. A motif within the T cell receptor alpha chain constant region connecting peptide domain controls antigen responsiveness. Immunity. 1996 November; 5(5):437-47) describe chimeric TCRs, whose points of fusion are positioned beyond the terminal intra chain—cysteines, and, in particular, are related to a motif of the "alpha chain connecting peptide domain", FETDxNLN. Both regions of mutations are positioned closely to the transmembrane domain, i.e. far away from the point mutations being described here as essential. Reciprocal amino acid exchanges (knob-hole) are not made.

Li et al. (Li Z G, Wu W P, Manolios N. Structural mutations in the constant region of the T-cell antigen receptor (TCR) beta chain and their effect on TCR alpha and beta chain interaction. Immunology. 1996 August; 88(4):524-30 and WO 97/47644 and WO 96/22306 describe the analysis of pairing of TCRs. The pairing is analyzed by immune precipitation and 2D-gel electrophoresis with a previous metabolic labeling of the chains. The authors created chimeric betaTCR to a molecule being immunologically irrelevant, and determined, whether these chimera, having different lengths but still corresponding to the wild type of the beta-chain, paired with the alpha-chain. The chimeras comprise different regions of, in particular, the constant domain, but do not indicate the point mutations that are described in the context of the present invention. The pairing-properties are neither examined under the effect of the mutagenesis on both chains nor in the context of a steric inversion (knob-hole).

The authors, nevertheless, draw two conclusions that are very important for the invention: On the one hand, the constant domain is critically responsible for the pairing, whereat, in particular, the region $Ser_{188}$-$Leu_{213}$ of betaTCR which particularly contains many basic amino acids ($arginine_{208}$ or $arginine_{195}$ of the 1, respectively), and is likely to be essential for the pairing, would be of interest. Nevertheless, the publication does not elaborate on this.

It was already attempted to resolve the problem of the specific manipulation of the interaction of the molecule by sterically complementary groups (Belshaw et al., Angew. Chem. Int. Ed. Engl. 34 (1995), 2129-2132); and this was exemplified based on antibodies (WO 96/27011; Atwell et al., 1997; Carter, 2001): for this, the heavy chains of two different antibodies of a different epitope-specificity should specifically pair one with the other, by sterically inverting contacting amino acid side chains at the contact position of both chains in their steric distribution in space: one small amino acid being present in the wild type interacting with an amino acid with a large side chain of the other chain is genetically mutated to an amino acid with a large side chain, whereas the large amino acid partner is exchanged into a small residue (English: "knob-hole"-model). In case of the pairing of chains of both mutated chains, again a small and a large amino acid again do meet each other, nevertheless with a steric inversion. If the direct periphery of the point mutants should allow for this steric exchange, the actual functionality of the heterodimeric molecule (that is, the epitope-recognition) should not be affected. WO 96/27011 describes bispecific antibodies, immune adhesines or chimeras thereof. This approach, nevertheless, completely ignores the additional control of the interaction of surfaces by the introduction of charge differences, and therefore is also only a 1-parametric concept. In the approach as described herein, a strict combinatorial 2-parametric concept is presented which takes into account both the sterics as well as the charge, and therefore implies that a 1-parametric approach in many objects does not comparably effectively manipulate the chain-pairing in the desired manner. The "knob hole"-model and the model "compensatory introduction of exposed charge carriers" being described herein thus are to be regarded as independent strategies. In addition, the latter model gives significantly more opportunities regarding the choice of the mutations to be introduced, and therefore a broader spectrum of possible solutions.

Atwell et al. sought to produce bispecific antibodies by linking the two halves of epitope-different antibodies one with the other at their contact positions ($CH_3$-domain) of the heavy chains (by "knob-hole"). In doing so, there are essential differences compared to the present invention which are to be taken into account for a transfer of the principle from antibodies to TCRs. In contrast to the monovalent TCR, an antibody is bivalent. The result is a structurally heterodimeric antibody that recognizes two different epitopes (bispecific). The approach according to the invention takes another direction: here, it is tried to selectively link the two predestinated chains of a monospecific TCR, in order to not generate functionally heterodimeric TCRs having potentially monospecificities that divert from the monospecificity as desired. The selection of the amino acids to be exchanged occurred according to the invention by "rational design": for this existing crystal structures of TCRs were studied by means of structure-representing software, and amino acid candidates were determined for punctual mutagenesis. The quality of the amino acid exchanges (anticipating the set of 20 codogenic natural amino acids in mammals) was each individually assessed according to steric circumstances as present in interacting amino acid pairs, respectively, by taking into account the surrounding of directly neighboring amino acids. The model system that was established in order to study the effect of the point mutants is described in more detail below.

Therefore, the method for rational mutagenesis of TCR according to the invention is neither disclosed nor proposed by the above mentioned publications as well as in the residual literature. The point mutations in each chain that have been introduced according to the invention shall lead to the fact that preferentially the externally introduced TCR chains are pairing, and that no mixed pairs are formed with the endogenic chains of the T-cells. This is an essential contribution regarding the issue specificity and therefore safety of the T-cell response.

It has to be noted that, in contrast to the state of the art, point mutants are markedly lower immunogenic than introduced affinity-tags or "linkers" comprising several amino acids, such as provided by, e.g., the single chain-TCR concept. In addition, the point mutants are nearly identical to the wild type chains that, until now, do have the strongest functional effectivity. All TAA-specific TCR that have been developed and will be developed, whether of murine or possibly also human origin, which shall be used in future in the adoptive immunotherapy by gene transfer into human T-cells of tumor patients, can easily be provided including these mutations. Therefore, the presented approach could find a wide-spread use in the clinical application (Bolhuis et al., 1998; Cavazzana-Calvo et al., 2000).

In a variant of the method according to the invention the amino acids that are first introduced after the mutagenesis of the DNA-molecules are further suitably chemically modified. Additional mutations can also be introduced non-chemically, such as, for example, by genetically produced point mutations from "phage display", in order to thereby introduce a sterically projecting group or a sterically recessing group. This means that first an amino acid is introduced which functions as the initial basis for the projecting group that is finally present. Suitable modifications therefore are amino acid derivates that are modified by chemical means, such as, for example, methylation (e.g. α-methylvaline), amidation, in particular of the C-terminal amino acid using an alkyl amine (e.g. ethylamine, ethanolamine, and ethylendiamine), and modifications of an amino acid side chain, such as, for example, acylation of the ∈-amino group of lysine. Other amino acids that can be incorporated into the chain include any of the D-amino acids which correspond to the 20 L-amino acids that are commonly found in proteins, or iminio amino acids, rare amino acids, such as, for example hydroxylysine, or non-protein amino acids, such as, for example homoserine and ornithine. A modified chain can exhibit one or several of these derivates, and D-amino acids. The chain can be synthesized by a chemical method, in particular using an automated peptide synthesizer or can be produced by a recombinant method. Modifications of the C-terminus include esterification and lactone formation. N-terminal modifications include acetylation, acylation, alkylation, pegylation, myristylation, and the like.

Nevertheless, usually the amino acids that are introduced after the mutagenesis of the DNA-molecules with the method according to the invention will directly provide the sterically projecting, preferably charged and/or polar groups or the sterically recessing, preferably conversely charged and/or polar groups, without that a further modification is required. A particularly preferred mutagenesis method according to the invention leads to an exchange of the amino acids of the first by those of the second chain or vice versa, wherein the amino acids that are introduced by the mutagenesis of the DNA-molecules are selected in such a way that a reciprocal exchange of the amino acids at the surfaces of the interacting chains des TCR is achieved.

In the context of the present invention, by sterically recessing, preferably charged and/or polar group, any chemically group being attached to each of the chains to be mutated shall be understood which sterically occupies less space compared to its corresponding earlier present group, and preferably carries a full or the fraction of a full charge unit. A charge is introduced which is complementary to the sterically projecting charged and/or polar group, either in the recessed group itself, or the net charge of the cage surrounding the sterically projecting charged and/or polar group is reverted by introducing a charge, or by the removal of a charge in the respective group (FIG. 11). Thus, the amino acid that is introduced after the mutagenesis of the DNA-molecules which introduces a sterically recessing group compared to the initial sequence can be selected from glycine, serine, threonine, alanine, without being limited thereto. Here, serine and threonine are those recessed groups that by themselves carry a partial charge. The use of glycine and alanine implies the emphasis of the remaining net charge of the surrounding cage (e.g. partial charges of the peptide bonds in the protein-backbone). Similarly, in the context of the present invention, as sterically processing group any chemically group being attached to each of the chains to be mutated shall be understood which sterically occupies more space compared to its corresponding earlier present group, and preferably carries a full or the fraction of a full charge unit. Thus, the amino acid that is introduced after the mutagenesis of the DNA-molecules that introduces a sterically projecting group compared to the initial sequence can be selected from lysine, arginine, histidine, cysteine, glutamine, glutamate and tyrosine, without being limited thereto.

In another additional aspect of the present invention, in a method according to the invention at least two surfaces of a TCR-chain are simultaneously subjected to mutagenesis. Thereby, possibly a further controlled pairing characteristic of the corresponding TCR can be achieved by means of the accumulation of several mutations, such as, for example, an energetically stronger or less strong pairing kinetics, compared to the non-modified state. A method for optimizing interchanging effects of several surfaces is represented by the "phage-display" method.

According to a further method according to the invention, the surfaces that are accordingly involved in interchanging effects can be localized in the variable domains of the TCR-chains. The surfaces that are accordingly involved in interchanging effects can, nevertheless, also be localized in the constant domains of the TCR-chains. The localization of these modifications is, amongst others, dependent from the desired specification of the respective TCR and its specific interactions.

Thus, according to a particular method according to the invention, the domains of the TCR-chains to be mutated can be selected from mammalian, and there, in particular, from human and/or mouse domains. Thereby, particularly preferred is a mutagenesis according to the present invention, wherein the rational mutagenesis of the TCR-chains simultaneously leads to a humanization of the TCR. Therefore, this mutagenesis, amongst others, leads to an improved compatibility of the TCR.

Therefore, the present invention essentially provides the three components of:

a) The approach being independent from the "knob hole"-model, to introduce charge into the inside of the complementary chain by means of large steric groups and by small steric groups themselves or by the omission of charged groups, in order to arrive at a charge compensation of the introduced charge. This is a strictly 2-parametric approach. Here, for the first time, it was attempted to apply this model to the contact area between the heterodimeric chains of a monovalent TCR, whereas so far in antibodies these were referred to the contact area between the heavy chains of a bivalently structured antibody.

b) The experimentally novel of the present invention is the fact, that a pair of amino acids in the TCR, for which the described model is applicable (αTCR/$Gly^{192}$ and βTCR/$Arg^{208}$ of the MDM2(81-88)-specific TCR, FIG. 5) is determined, and the quality of the exchanges ($^{Arg}208^{Gly}$ and $^{Gly}192^{Arg}$) is defined. This is about a 1:1 inversion of the steric and charge-dependent situations as found, and corresponds to the transition from status I (wild type) to status II (1 mutation/chain) of FIG. 11 or 2, respectively: The introduced positive charge of the arginine is compensated by the residual carbonyles of the polypeptide fiber of the complementary chain. An additional indicator for a charge neutralization being comparable to the wild type is the modeling capacity being supported by the protein structure-database of hydrogen bridges between the guanidinium-group of the arginine and the carbonyles of the main chain both for status I as well as for II for the crystal structure of an also murine TCR (1.pdb of FIG. 6).

c) The pair of amino acids to be exemplary determined here should be chosen in such a manner that said pair can be generalized from one to all murine TCRs, in order to also provide future murine TCRs being specific for other TAAs with these mutations, and, on the other hand, can also be extended to human TCRs. The constant domain was chosen, since here a sufficient homology between human and murine TCR exists, in order to assume that the selected mutations do have a comparably detrimental effect for hybrid Hu/Mu TCR, as was exemplary shown for murine "hybrid" TCR in the present invention.

It has to be taken into account that other amino acid exchanges at the respective position can also have a comparable effect. Furthermore, an optimization through additional cumulating exchanges in the surrounding of the respective point mutations is conceivable.

A further aspect of the present invention relates to a method wherein the alpha- and beta-chains of a MDM2(81-88)-specific TCR are used as the alpha- and beta-chains, and wherein the $Gly_{192}$ of the constant region of the alpha-chain and the $Arg_{208}$ of the constant region of the beta-chain are exchanged by $Arg_{192}$ in the constant region of the alpha-chain and by $Gly_{208}$ in the constant region of the beta-chain. Based on this TCR, for the first time the principle according to the invention could successfully be applied.

Further preferred is a method according to the invention wherein a retroviral vector, in particular pBullet, is used as transfection system. In addition, IRES-elements can be used in said vectors.

A further aspect of the present invention relates to a mutated first (alpha-) or second (beta-) chain of a TCR that is produced according to a method according to the present invention. Further particularly preferred is a TCR that is mutated according to the invention, in particular a mutated MDM2(81-88)-specific TCR, wherein said TCR exhibits at least one mutated alpha- and beta-chain. This mutated TCR according to the present invention can also be present in form of a fusion protein, comprising the polypeptides modified according to the invention or parts thereof. The fusion protein can be characterized in that it comprises the 4-region of CD3 or CD8 or CD16 or parts thereof, in particular the ζ-region of human CD3 or CD8 or CD16 or parts thereof. In particular, the fusion protein according to the invention can comprise a fusion protein of the ζ-chain of the CD3-complex or ITAM-motifs of the ζ-chain or parts thereof, in particular the ζ-chain of human CD3 or parts thereof. The fusion protein can furthermore be characterized in that it comprises CD8α or the Lck-binding motif of CD8α or parts thereof, in particular of human CD8α.

A further aspect of the present invention relates to an isolated nucleic acid comprising a sequence encoding for a mutated first (e.g. alpha-) or second (e.g. beta-) chain of a TCR according to the invention. This nucleic acid according to the invention can be a DNA, RNA, PNA (peptide nucleic acid) or p-NA (pyranosyl nucleic acid), preferably a DNA, in particular a double-stranded DNA having a length of at least 8 nucleotides, preferably with at least 18 nucleotides, in particular with at least 24 nucleotides. The nucleic acid can be characterized in that the sequence of said nucleic acid exhibits at least one intron and/or a polyA-sequence. It can also be present in form of its antisense sequence.

A further aspect of the present invention relates to a DNA- or RNA-vector molecule which comprises at least one or several nucleic acid(s) according to the invention and which can be expressed in cells. For the expression of the respective gene, in general a double-stranded DNA is preferred, whereby the DNA-region encoding for the polypeptides is particularly preferred. This region starts with the first start-codon (ATG) being positioned in a Kozak consensus sequence (Kozak, 1987, Nucleic. Acids Res. 15:8125-48) up to the next stop-codon (TAG, TGA or TAA, respectively) that is positioned in the same reading frame to the ATG. A further use of the nucleic acid sequences according to the invention is the construction of anti-sense oligonucleotides (Zheng and Kemeny, 1995, Clin. Exp. Immunol. 100:380-2) and/or ribozymes (Amarzguioui, et al. 1998, Cell. Mol. Life. Sci. 54:1175-202; Vaish, et al., 1998, Nucleic Acids Res. 26:5237-42; Persidis, 1997, Nat. Biotechnol. 15:921-2). Using anti-sense oligonucleotides, one can reduce the stability of the nucleic according to the invention and/or inhibit the translation of the nucleic according to the invention. Thus, for example, the expression of the respective gene in cells can be reduced in vivo as well as in vitro. Therefore, oligonucleotides can be suitable as therapeutics. This strategy is, for example, suitable also for skin, epidermal and dermal cells, in particular, if the antisense oligonucleotides are complexed with liposomes (Smyth et al., 1997, J. Invest. Dermatol. 108: 523-6; White et al., 1999, J. Invest. Dermatol. 112:699-705). A single-stranded DNA or RNA is preferred for use as a probe or as "antisense" oligonucleotide.

In addition to the natural nucleic acids that have been isolated from cells, all nucleic acids according to the invention or their parts can also be produced synthetically. Furthermore, in order to work the invention, a nucleic acid can be used that has been synthetically produced. Thus, for example, the nucleic acid according to the invention can be chemically synthesized based on the protein sequences as described by reference to the genetic code e.g. according to the phosphotriester-method (see, e.g. Uhlmann, E. & Peyman, A. (1990) Chemical Reviews, 90, 543-584).

In general, oligonucleotides are rapidly degraded by endo- or exonucleases, in particular by DNases and RNases that are present in cells. It is therefore advantageous to modify the nucleic acid in order to stabilize them against the degradation, such that a high concentration of the nucleic acid in the cell is maintained over a long time period (WO 95/11910; Macadam et al., 1998, WO 98/37240; Reese et al., 1997, WO 97/29116). Typically, such stabilization can be achieved by introducing one or several internucleotide-phosphorous groups or by introducing one or several non-phosphorous-internucleotides.

Suitably modified internucleotides are summarized in Uhlmann and Peymann (1990 Chem. Rev. 90, 544) (WO 95/11910; Macadam et al., 1998, WO 98/37240; Reese et al., 1997, WO 97/29116). Modified internucleotide-phosphate residues and/or non-phosphorous bridges in a nucleic acid that can be employed in a use according to the invention, for example, contain methyl phosphonate, phosphorothioate, phosphoramidate, phosphorodithioate, phophatester, whilst non-phosphor-internucleotide-analogs, for example, contain siloxane bridges, carbonate bridges, carboxymethylester, acetamidate bridges, and/or thioether bridges. It is further intended that these modifications improve the shell-life of a pharmaceutical composition which can be employed in a use according to the invention.

A further aspect of the present invention relates to a vector, preferably in form of a plasmid, shuttle vector, phagemid, cosmid, expression vector, adenoviral vector, retroviral vector (Miller, et al. "Improved retroviral vectors for gene transfer and expression", BioTechniques Vol. 7, No. 9, p 980, 1989) and/or gene-therapeutically effective vector containing a nucleic acid according to the invention.

Thus, the nucleic acid according to the invention can be contained in a vector, preferably in an expression vector or gene-therapeutically effective vector. Preferably, said gene-therapeutically effective vector contains T-cell specific regulatory sequences that are operatively linked with the nucleic acid according to the invention. The expression vectors can be prokaryotic or eukaryotic expression vectors. Examples for prokaryotic expression vectors are e.g. the vectors pGEM or pUC-derivates for the expression in *E. coli* and for eukaryotic expression vectors e.g. the vectors p426Met25 or p426GAL1 (Mumberg et al. (1994) Nucl. Acids Res., 22, 5767-5768) for the expression in *Saccharomyces cerevisiae*, e.g. Baculovirus-vector, such as disclosed in EP-B1-0 127 839 or EP-B1-0 549 721 for the expression in insect cells, and e.g. the vectors Rc/CMV, and Rc/RSV or SV40-vectors that are commonly available for the expression in mammalian cells.

In general, the expression vectors do also contain promoters that are suitable for the respective host cell such as, for example, the trp-promoter for the expression in *E. coli* (see, e.g., EP-B1-0 154 133), the Met 25, GAL 1 or ADH2-promoter for the expression in yeasts (Russel et al. (1983), J. Biol. Chem. 258, 2674-2682; Mumberg, supra), the baculovirus-polyhedrin-promoter for the expression in insect cells (see, e.g., 13. EP-B1-0 127 839). For the expression in mammalian cells, for example, promoters are suitable that allow for a constitutive, controllable tissue specific, cell cycle specific or metabolically specific expression in eukaryotic cells. Controllable elements according to the present invention are promoters, activator sequences, enhancers, silencers and/or repressor sequences. Examples for suitable controllable elements that allow for the constitutive expression in eukaryotes are promoters that are recognized by the RNA polymerase III or viral promoters, CMV-enhancers, CMV-promoters, CMV-LTR-hybrids, SV40 promoters or LTR-promoters e.g. from MMTV (mouse mammary tumor virus; Lee et al. (1981) Nature 214, 228-232), and additional viral promoter and activator sequences derived from, for example, HBV, HCV, HSV, HPV, EBV, HTLV or HIV. One example for a controllable element that allows for a controllable expression in eukaryotes is the tetracycline operator in combination with a corresponding repressor (Gossen M. et al. (1994) Curr. Opin. Biotechnol. 5, 516-20).

Examples for controllable elements that allow for the T-cell specific expression in eukaryotes are promoters or activator sequences from promoters or enhancers of those genes that code for proteins that are only expressed in these types of cells.

Examples for controllable elements that allow for the cell cycle specific expression in eukaryotes are promoters of the following genes: cdc25, Cyclin A, Cyclin E, cdc2, E2F, B-myb or DHFR (Zwicker J. and Müller R. (1997) Trends Genet. 13, 3-6). Examples for controllable elements that allow for the metabolically specific expression in eukaryotes are promoters that are regulated by hypoxia, by glucose starvation, by concentration of phosphate or by heat shock.

The vector according to the invention can be used for the transfection of a host cell that is preferably a T-cell. Particularly preferred is a host cell which is characterized in that it expresses a polypeptide or fusion protein according to the invention on its surface. An additional object of the invention therefore relates to a method for producing a polypeptide for the diagnosis and/or treatment of diseases that are related to oncoproteins or for identifying pharmacologically active substances in a suitable host cell, which is characterized in that a nucleic acid according to the invention is suitably expressed.

Thus, for example the polypeptide is produced according to methods that are generally known to the person of skill, by expressing of the nucleic acid according to the invention in a suitable expressions system, as already described above. As host cells, for example, the *E. coli* strains DHS, HB101 or BL21, the yeast strain *Saccharomyces cerevisiae*, insect cell lines, e.g. from *Spodoptera frugiperda* or the animal cells COS, Vero, 293, HaCaT, and HeLa can be used, which are all commonly available.

In order to allow for the introduction of nucleic acids according to the invention and thereby the expression of the polypeptide in a eu- or prokaryotic cell by transfection, transduction, transformation or infection the nucleic acid can be present as plasmid, as a part of a viral or non-viral vector or particle. Here, particularly suitable as viral vectors or particle are: baculoviruses, vacciniaviruses, retroviruses, adenoviruses, adeno-associated viruses, and herpes viruses. As non-viral carrier, in particular: virosomes, liposomes, cationic lipids or poly-lysine conjugated DNA are suitable.

Examples of gene-therapeutically effective vectors are viral vectors, for example adenoviral vectors or retroviral vectors (Lindemann et al., 1997, Mol. Med. 3: 466-76; Springer et al., 1998, Mol. Cell. 2: 549-58; Weijtens et al. "A retroviral vector system, 'STITCH'; in combination with an optimized single chain antibody chimeric receptor gene structure allows efficient gene transduction and expression in human T-lymphocytes", Gene Therapy (1998) 5, 1995-1203).

A preferable mechanism in order to bring about expression of polypeptides according to the invention in vivo is the viral genetic transfer, in particular with the aid of retroviral particles. These are preferably used in order to provide respective target cells of the patient, preferably T-lymphocytes, ex vivo with the genes or nucleotide sequences that encode for polypeptides according to the invention by transduction. Subsequently, the target cells can be reinfunded into the patient in the sense of an adoptive cellular transfer in order to take over tumoricidal and/or immunomodulating effector functions with the de novo introduced specificity. Recently, using this way, very promising gene-therapeutical successes in the treatment of SCID-X1-disease in newborn being characterized by an immune incompetence were achieved, wherein hematological precursor cells were retrovirally provided with an analogous intact transgen of a non-functionally mutated variant of a gene for the γ-chain present in infants that is essential for the differentiation in the different effector cells of the adaptive immune system (Cavazzana-Calvo et al., 2000).

Furthermore, the possibility exists to perform the genetic transfer in vivo, on the one hand by preferentially stereotactic injection of the infectious particles on the other hand by direct application of virus-producing cells (Oldfield, et al. Hum. Gen. Ther., 1993, 4:39-69).

The viral vectors that are commonly used for the transfer of genes in accordance with the current state of the art are primarily retroviral, lentiviral, adenoviral and adeno-associated viral vectors. These are circular nucleotide sequences that are derived from natural viruses, wherein at least the viral structural protein encoding gene has been replaced by the construct to be transferred.

Retroviral vector systems provide the condition for a long lasting expression of the transgene by the stable but uncontrolled integration into the genome of the host. Vectors of the younger generation have no irrelevant and potentially immunogenic proteins, furthermore, there is no previous immunity of the acceptor against the vector. Retroviruses contain an RNA-genome that is packaged into a lipid envelope that consists of parts of the cellular membrane of the host and viral proteins. For the expression of viral genes the RNA-genome is reversely transcribed and integrated into the DNA of target cell with the enzyme integrase. Then, the genes can be transcribed and translated by the infected cell, whereby viral parts are generated that assemble to form retroviruses. Only at this time the RNA is introduced into the newly generated viruses. The genome of retroviruses has three essential genes: gag, that encodes for viral structural proteins, so-called group specific antigens, poi for enzymes such as reverse transcriptase and integrase, and env for the envelope protein ("envelope"), that is responsible for the binding of the host-specific receptor. After transfection, the production of the replication incompetent viruses takes place in so-called packaging cell lines, that have been additionally provided with the gag/pol-encoding genes, and express these "in trans", and therefore complement the formation of replication incompetent (i.e. gag/pol-deleted) transgenic viral particles. An alternative is the co-transfection of the essential viral genes, whereby only the vector containing the transgenes carrying the packaging signal.

The separation of these genes on the one hand enables any combination of the gal/pol-reading frame with env-reading frames obtained from different strains, whereby pseudotypes with modified host tropism are generated, on the other hand thereby the formation of replication competent viruses inside packaging cells can be drastically reduced. The envelope protein derived from "gibbon ape leukemia virus" (GALV) that is used in the "stitch" or "bullet"-vector system, respectively, has the ability to transduce human cells, and is established in the packaging cell line PG13 with an amphotrophic host region (Miller et al., 1991). In addition, the safety is increased by a selective deletion of non-essential viral sequences for preventing a homologous recombination and thus increases the production of replication competent particles.

Novel non-viral vectors consist of autonomous non self-integrating DNA-sequences, the transposons, that are introduced by e.g. liposomal transfection into the host cell, and have for the first time been successfully employed for the expression of human transgenes in mammalian cells (Yant et al., 2000).

Gene-therapeutically effective vectors can be obtained by complexing the nucleic acid according to the invention with liposomes, since thereby a very high transfection efficiency, in particular of skin cells, can be achieved (Alexander and Akhurst, 1995, Hum. Mol. Genet. 4: 2279-85). Excipients, that increase the transfer of nucleic acids into the cell, can be, for example, proteins or peptides that are bound to DNA, or synthetic peptide-DNA-molecules, that allow for the transport of the nucleic acid into the nucleus of the cell (Schwartz et al. (1999) Gene Therapy 6, 282; Brandén et al. (1999) Nature Biotech. 17, 784). Excipients also include molecules that allow for a release of nucleic acids into the cytoplasm of the cell (Planck et al. (1994) J. Biol. Chem. 269, 12918; Kichler et al. (1997) Bioconj. Chem. 8, 213) or, for example, liposomes (Uhlmann and Peymann (1990) supra). Another particularly suitable form of the gene-therapeutical vectors can be obtained by attaching the nucleic acids according to the invention onto gold particles, and shooting these into tissue, preferably into the skin, or cells with the aid of the so-called "gene gun" (Wang et al., 1999, J. Invest. Dermatol., 112:775-81).

For the gene-therapeutical use of the nucleic acid according to the invention it is also advantageous if the part of the nucleic acid encoding for the polypeptide contains one or several non coding sequences, including intron sequences, preferably between promoter and the start codon of the polypeptide, and/or a polyA-sequence, in particular the naturally occurring polyA-sequence or an SV40 virus polyA-sequence, in particular at the 3'-end of the gene, since thereby a stabilization of the mRNA can be achieved (Jackson, R. J. (1993) Cell 74, 9-14 and Palmiter, R. D. et al. (1991) Proc. Natl. Acad. Sci. USA 88, 478-482).

An additional aspect of the present invention relates to a host cell, that contains a DNA- or RNA-vector molecule according to the invention. This in particular can be a T-cell that is transformed with a vector according to the invention or another genetic construct according to the invention. Host cells can be prokaryotic as well as eukaryotic cells, examples for prokaryotic host cells are *E. coli* and for eukaryotic cells are *Saccharomyces cerevisiae* or insect cells.

Therefore, an additional aspect relates to a recombinant T-cell that expressed at least one mutated TCR according to the present invention. A particularly preferred transformed host cell is a transgenic T-precursor cell or a stem cell that is characterized in that it comprises a genetic construct according to the invention or an expression cassette according to the invention. Methods for transformation or transduction of host cells and/or stem cells are well known to the person of skill, and, for example, include electroporation or microinjection. A particularly preferred transformed host cell is a patient-unique T-cell, that is after the extraction transfected with a genetic construct according to the invention. According to the invention, host cells in particular can be obtained by extracting one or several cells, preferably T-cells, in particular $CD8^+$-T-cells that are subsequently transfected or transduced ex vivo with one or more genetic constructs according to the invention, in order to thereby obtain host cells according to the invention. Then, the ex vivo generated specific T-cells can subsequently be reimplanted into the patient. The method therefore is similar to the method described by Darcy et al. ("Redirected perforin-dependent lysis of colon carcinoma by ex vivo genetically engineered CTL" J. Immunol., 2000, 164: 3705-3712) by using scFv anti-CEA receptor transduced CTL, perforin, and γ-IFN.

The modified (poly)peptide and their derivatives according to the invention for example can be used for the active and/or passive immunization of patients with diseases, in particular timorous diseases that for example are related to MDM2. A particularly preferred aspect of the present invention therefore relates to the use, wherein a cancerous disease is treated, in particular a cancerous disease, that is related to a modified expression of MDM2, in order to achieve the induction, production, and increase of oncogen-specific, e.g. MDM2-specific CTL, and to specifically kill the tumor- and leukemic cells of the respective patient. Such diseases, for example, include solid timorous diseases, lymphohematopoeitic neoplasia, malign hematological diseases, also in form of a multiple myeloma (or plastocytoma), a histiocytic lymphoma and a burst of CML-blasts. Respective related TAAs against which the corresponding TCRs can be developed are, for example, p53, Her-2/neu, Ras, tyrosinase, MART, Gp100, MAGE, BAGE, MUC-1, CD45, CD19, and PRD1-BF1.

A particularly preferred aspect of the present invention therefore in addition relates to a composition, in particular a pharmaceutical composition that comprises a recombinant T-cell according to the present invention. Furthermore, preferred is the use of a mutated alpha- or beta-chain of a TCR according to the present invention, of a mutated TCR according to the present invention, and/or a recombinant T-cell according to the present invention for the production of therapeutics and/or prophylactics for the treatment of cancerous diseases. In a particularly preferred manner of the treatment, one or more cells, preferably I-cells, in particular $CD8^+$-T-cells are extracted from the patient that are subsequently transduced or transfected ex vivo with one or several genetic constructs according to the invention. Then, the ex vivo generated specific T-cells subsequently can reimplanted into the patient. The composition according to the invention furthermore can further contain suitable additives and excipients.

An object of the present invention is also a medicament for the indication and therapy of diseases associated with oncoprotein-protein, containing a nucleic acid according to the invention or a polypeptide according to the invention and, optionally, containing suitable additives and excipients, as well as a method for producing of such a medicament for the treatment of diseases associated with oncoprotein-protein, wherein a nucleic acid according to the invention or a polypeptide according to the invention is formulated with a pharmaceutically acceptable carrier. Therapeutics and/or prophylactics prophylactics, in particular vaccines, recombinant particles or solutions for injection or infusion can be considered that contain (a) the TCR-receptor polypeptide according to the invention and/or its derivatives and/or (b) a nucleic acid according to the invention as active ingredient, and/or (c) T-lymphocytes generated in vitro or ex vivo that contain a specific mutated TCR being directed against Oncoprotein.

For the gene therapeutical use in humans in particular a medicament and/or recombinant particle is suited that contains the nucleic acid according to the invention in naked form or in form of one of the above described gene-therapeutically effective vectors or in a form complexed with liposomes or gold particles respectively. The pharmaceutical carrier, for example, is a physiological buffer solution, preferably having a pH of about 6.0-8.0, preferably of about 6.8-7.8, in particular of about 7.4 and/or of an osmolarity of about 200-400 milliosmol/liter, preferably of about 290-310 milliosmol/liter. In addition the pharmaceutical carrier can contain suitable stabilizers, such as, for example, nuclease inhibitors, preferably complexing agents such as EDTA and/or other excipients known to the person of skill.

The term "coding nucleic acid" refers to a DNA-sequence encoding for a isolatable bioactive polypeptide according to the invention or a precursor. The polypeptide can be encoded by a sequence in its complete length or any part of the coding sequence as long as the specific, for example, enzymatic activity is preserved.

It is known that small modifications can be present in the sequence of the nucleic acids according to the invention, for example by the degeneration of the genetic code, or that non-translated sequences can be attached to the 5' and/or 3'-end of the nucleic acid, without its activity being essentially modified. Therefore, this invention also encompasses so-called "functional variants" of the nucleic acids according to the invention.

With the term "functional variants" all DNA-sequences are designated that are complementary to a DNA-sequence that hybridizes under stringent conditions with a reference sequence derived therefrom or parts thereof, in particular the hypervariable V(D)JC-region, and have activity that is similar or identical to the corresponding polypeptide according to the invention.

By "stringent hybridization conditions" those conditions are to be understood, wherein a hybridization occurs at 60° C. in 2.5×SSC-buffer, followed by several washing steps at 37° C. in a lower buffer concentration and maintains stable.

With the term "functional variants" in the sense of the present invention polypeptides are to be understood that are functionally related to the polypeptides according to the invention, i.e. have structural features of the polypeptides. Examples of functional variants are the corresponding polypeptides that are stemming from other organisms as the mouse, and also human, preferably from non-human mammals such as, for example, monkeys, porcine and rat. Other examples of functional variants are polypeptides that are encoded by different alleles of the gene in different individuals or in different organs of an organism. Encompassed by the present invention are, in particular, also functional TCR-variants that recognize the identical epitope of the MDM2-polypeptide and trigger a specific T-cell response.

In a further sense also polypeptides are to be understood that have a sequence homology, in particular a sequence identity, of about 70%, preferably about 80%, in particular about 90%, more particularly about 95% to the polypeptides having the amino acid sequence according to one of the SEQ ID No. 1 to SEQ ID No. 6 and/or to the DNA sequences that are derived from the peptide sequences. Among those are also additions, inversions, substitutions, deletions, insertions or chemical/physical modifications and/or exchanges or parts of the polypeptide in a size of about 1-60, preferably of about 1-30, in particular of about 1-15, more particularly of about 1-5 amino acids. For example, the first amino acid methionine can be missing without that the function of the polypeptide is essentially modified.

The invention shall now be further explained based on the accompanying Examples and Figures without being limited by these.

SEQ. ID No. 1: shows the alpha-chain of the murine TCR 1 (1TCR_aTCR.pro),

SEQ. ID No. 2: shows the alpha-chain of the murine MDM2 TCR (Mu_Wt_aTCR_MDM2.pro), SEQ. ID No. 3: shows the alpha-Chain of the human TCR 1bd2 (1bd2_a.pro), SEQ. ID No. 4: shows the beta-Chain of the murine TCR 1 (1TCR_bTCR.pro), SEQ. ID No. 5: shows the beta-Chain of the murine MDM2 TCR (Mu_Wt_bTCR_MDM2.pro), and SEQ. ID No. 6: shows the beta-Chain of the human TCR 1bd2 (1bd2_b.pro).

Figure 1:
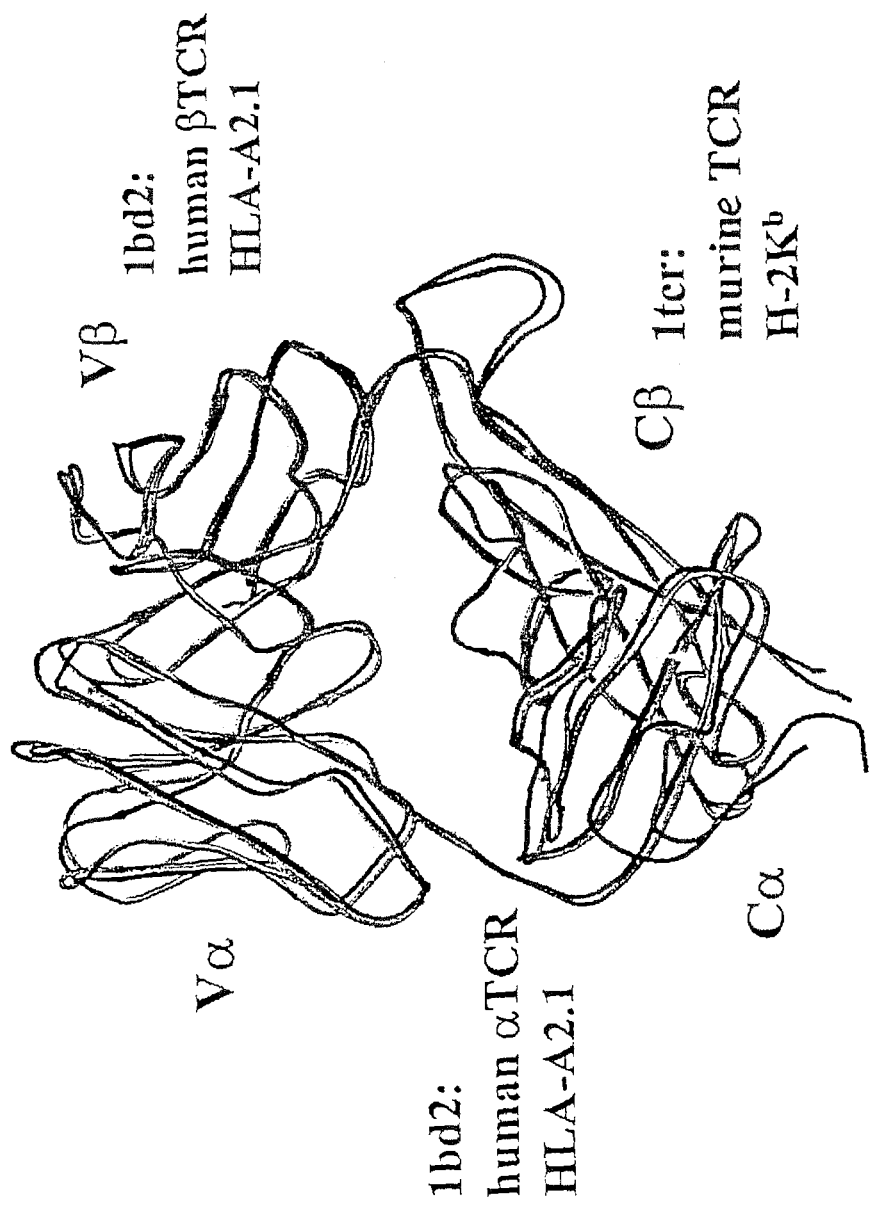

FIG. 1 shows the superposition of the protein backbone of protein crystal structures of a murine $H2-K^b$-restringated (1, Garcia et al, 1998) and a human HLA-A2-restringated (1bd2, Ding et al., 1998) T-cell-receptor. The heterodimeric human TCR is depicted in dark grey (αTCR) and light gray (βTCR) for the respective chains, the murine TCR for the single chains is gray in total.

FIG. 2 shows the representation of the protein backbone of 1, with exclusively those side chains that are identical to 1bd2. The upper graphic illustrates the presence of few identical residues in the contact area of the variable domains (Vα, Vβ) of both chains. The lower graphic is turned around the axes in the paper-plain in such a manner that it documents the numerous presences of identical amino acids in the contact area of the constant domains (Cα, Cβ).

Figure 3:
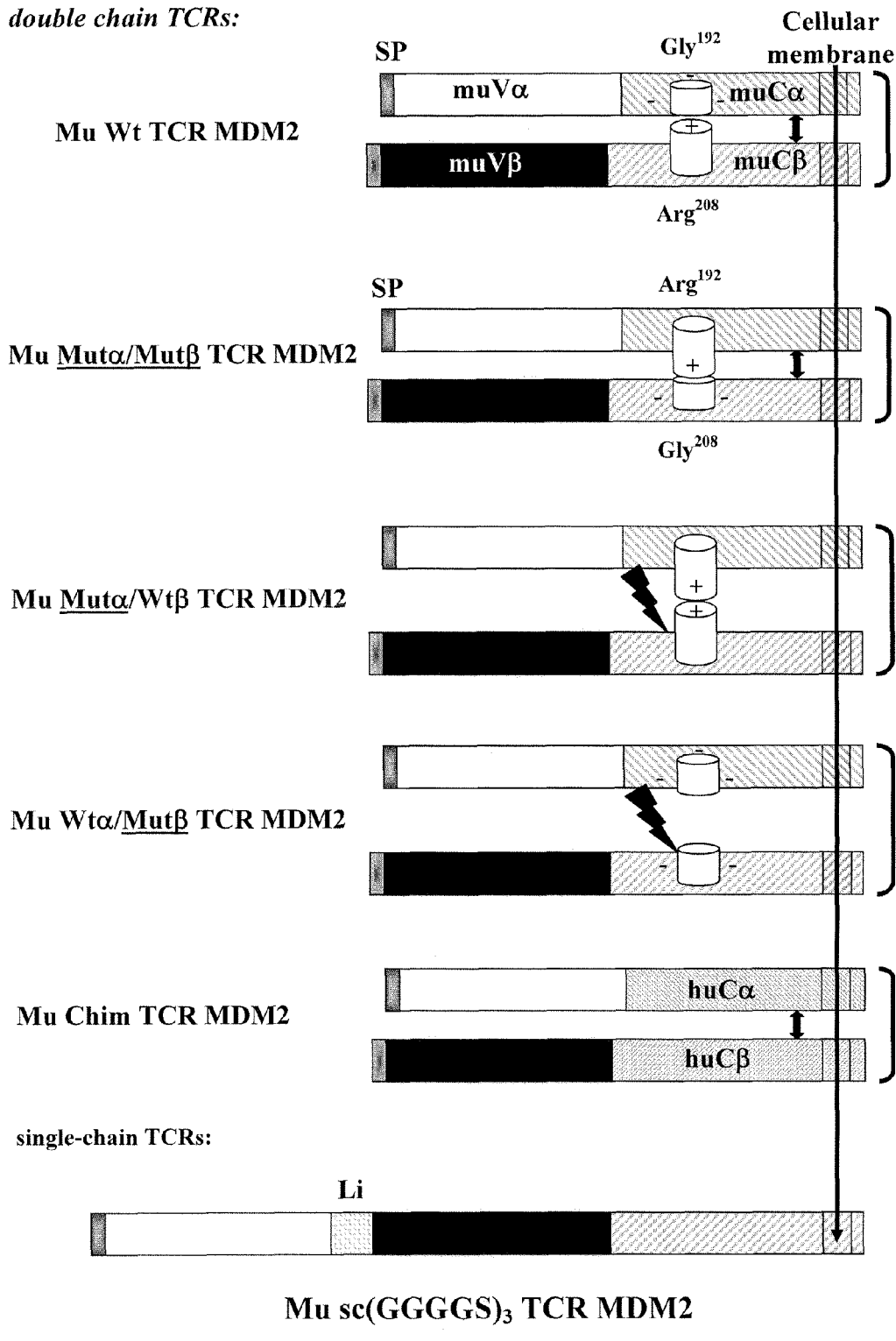

FIG. 3 shows the representation of relevant MDM2(81-88)-specific TCR-constructs, from which in the murine model that is presented the respective wild type chains (Wt) of the Mu Wt TCR MDM2 were mutated (Mut) in correspondence with the graphics, and were combined in murine T-cells after retroviral transfer. The murine variable domains are white, the constant domains are hatched. The partially humanized TCR (Mu Chim TCR MDM2) exhibits a tighter hatching in the constant domain. Below, a single chain TCR is depicted whose variable domains are linked via a (GlyGlyGlyGlySer)$_3$-linker. The length of the cylinder indicated the relevant amino acid positions and their sterical sizes. The lightning bolt symbolizes the absence of the interaction of the chains due to sterical interference (Mu Mutα/Wtβ TCR MDM2) or the absence of interaction (Mu Wtα/Mutβ TCR MDM2) of the respective pairs of amino acids.

FIG. 4 shows the amino acid sequence alignment of the murine TCR 1 (1TCR_aTCR.pro (SEQ ID NO:1) or 1TCR_bTCR.pro (SEQ ID NO:4), respectively), for which the structural data was present with the MDM2-specific TCR (Mu_Wt_aTCR_MDM2.pro (SEQ ID NO:2) and Mu_Wt_bTCR_MDM2.pro (SEQ ID NO:5), respectively) and the alpha-chain of human TCR 1bd2 1bd2_a.pro (SEQ ID NO:3), and the beta-chain of human TCR 1bd2_b.pro (SEQ ID NO:6) for which likewise structural date was present. The heights of the bars indicate the extent of the identity as found at the respective positions. From these, it can be taken that the amino acids that are immediately surrounding the mutated amino acids and largely are interacting therewith are mostly conserved between human and mouse. The analysis of the crystal structures indicated insignificant differences. FIG. 4a: α-chains-comparison; FIG. 4b: β-chains-comparison.

Figure 5:
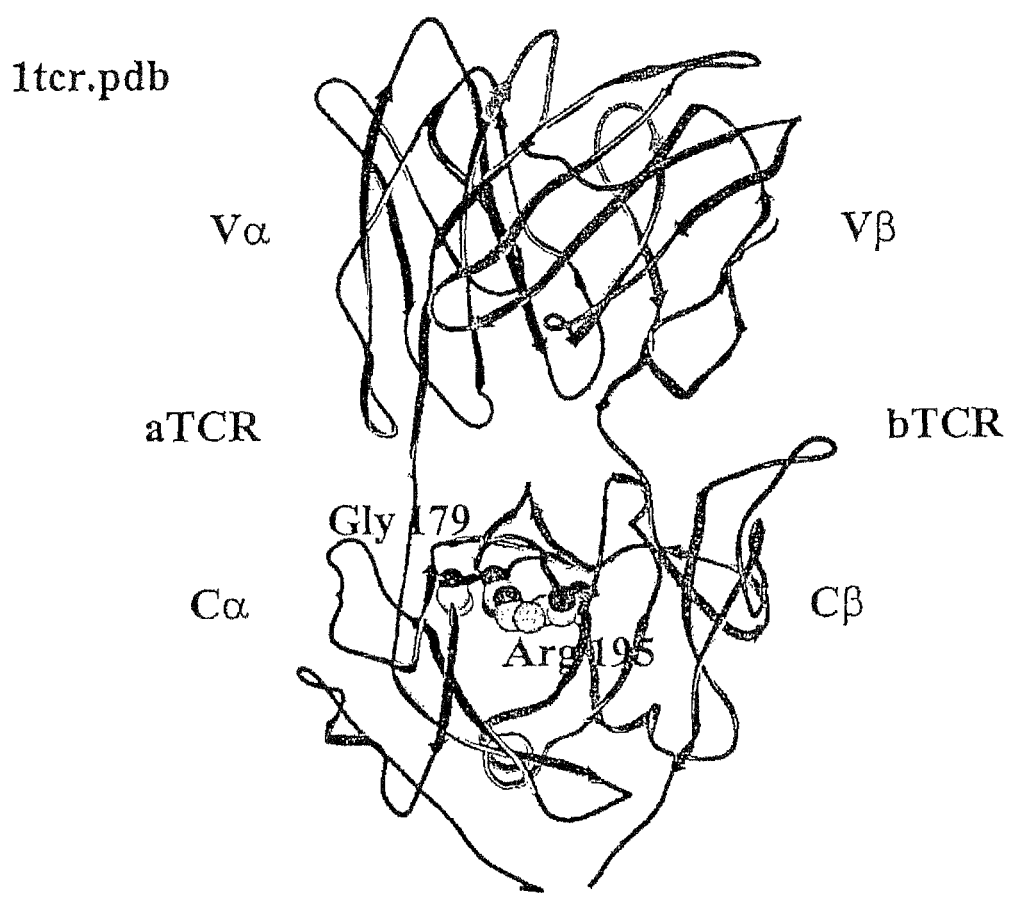

FIG. 5 shows the indication of the amino acid pairs in the structurally whole context of 1, corresponding to the mutated amino acid pair $Gly^{192}/Arg^{208}$ of MDM2-specific TCR. The amino acids are intermediately positioned in the drilled β-sheets of both chains within the constant domains that are wound one around the other and are aligned one to each other. For orientation, the relevant CDR3-loops of the variable domains that recognize the peptide antigen of 1 are shaded in a diverging shade of gray: the affected pair of amino acids is positioned far away from the region that is responsible for the binding of the MHC-peptide-complexes.

Figure 6:
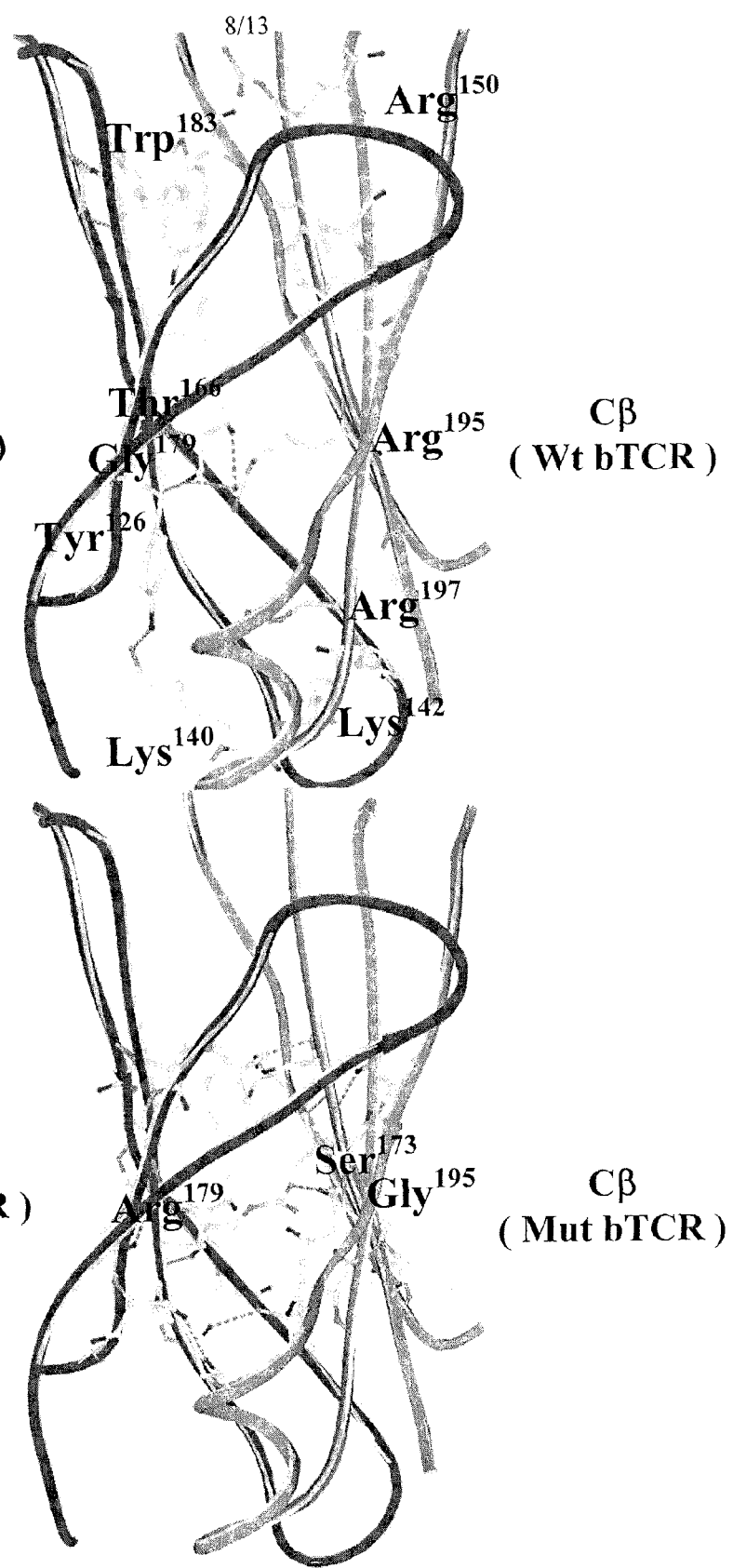

FIG. 6 shows the sterical depiction of the wild type amino acid pair $Gly^{179}/Arg^{195}$ (FIG. 6a) and the mutated amino acid pair $Arg^{179}/Gly^{195}$ (FIG. 6b) of the 1.pdb as can be found for the latter following structural data-supported design. FIG. 6a includes those amino acids of the central β-sheets having large sterical side chains, in contrast FIG. 6b includes those amino acids in a spherical region of a diameter of 5 Angstroms around the Cα of the $Arg^{179}$ that was mutated on the screen by omitting those side chains that point away from the contact region of the chains (for reasons of simplicity). A conformer was chosen that does not have an affecting interaction with the neighboring side chains. The stretched conformation enables the formation of an H-bridge to the corresponding main-chain-oxygen of the β-chain in near analogy to the situations in wild type (FIG. 6a).

Figure 7:
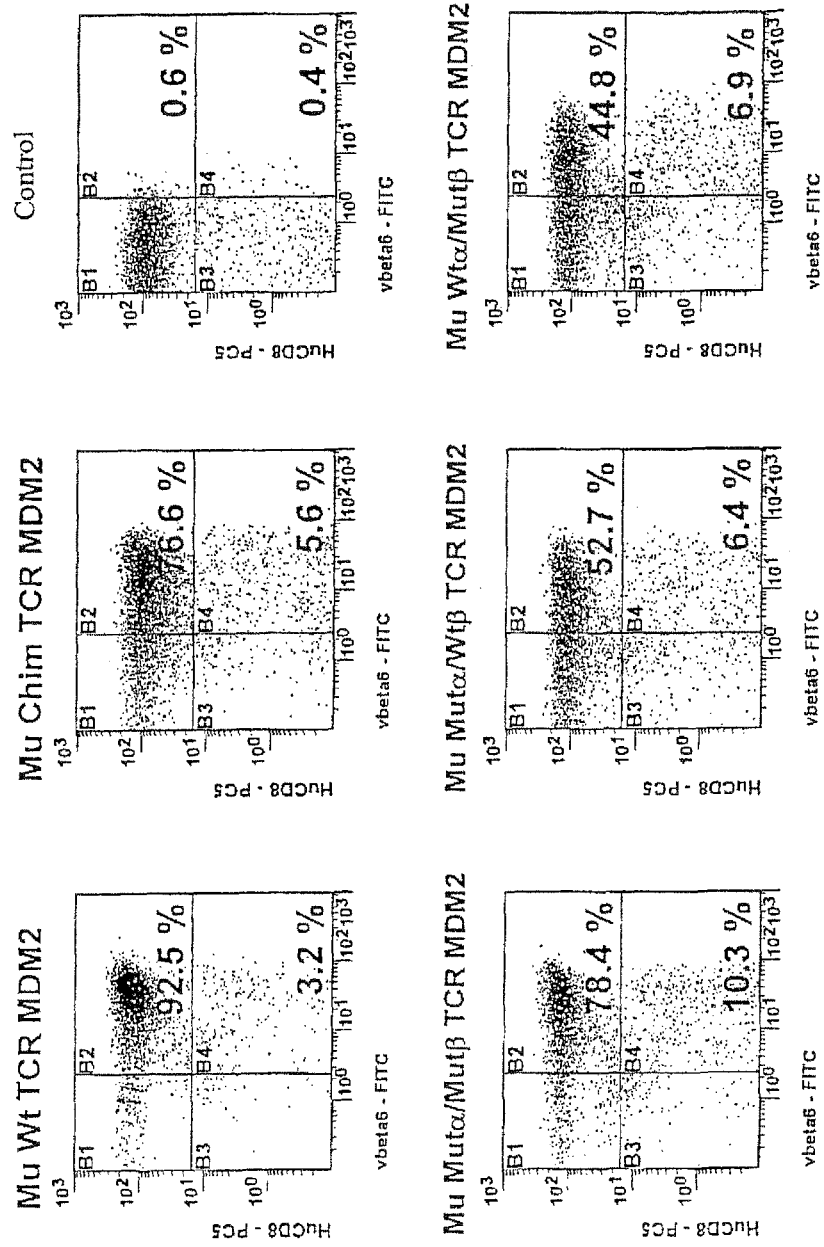

FIG. 7 shows the FACS-analysis of the human transduced T-cells that each was provided with the different combinations of the TCR-constructs described in FIG. 3. Depicted is a 2-fold staining of vβ6-FITC and CD8-PC5: only CD8-positive transduced T-cells show the desired cytotoxic effector function. The vβ6-staining allows for the determination of β-chain but not for the α-chain.

Figure 8:
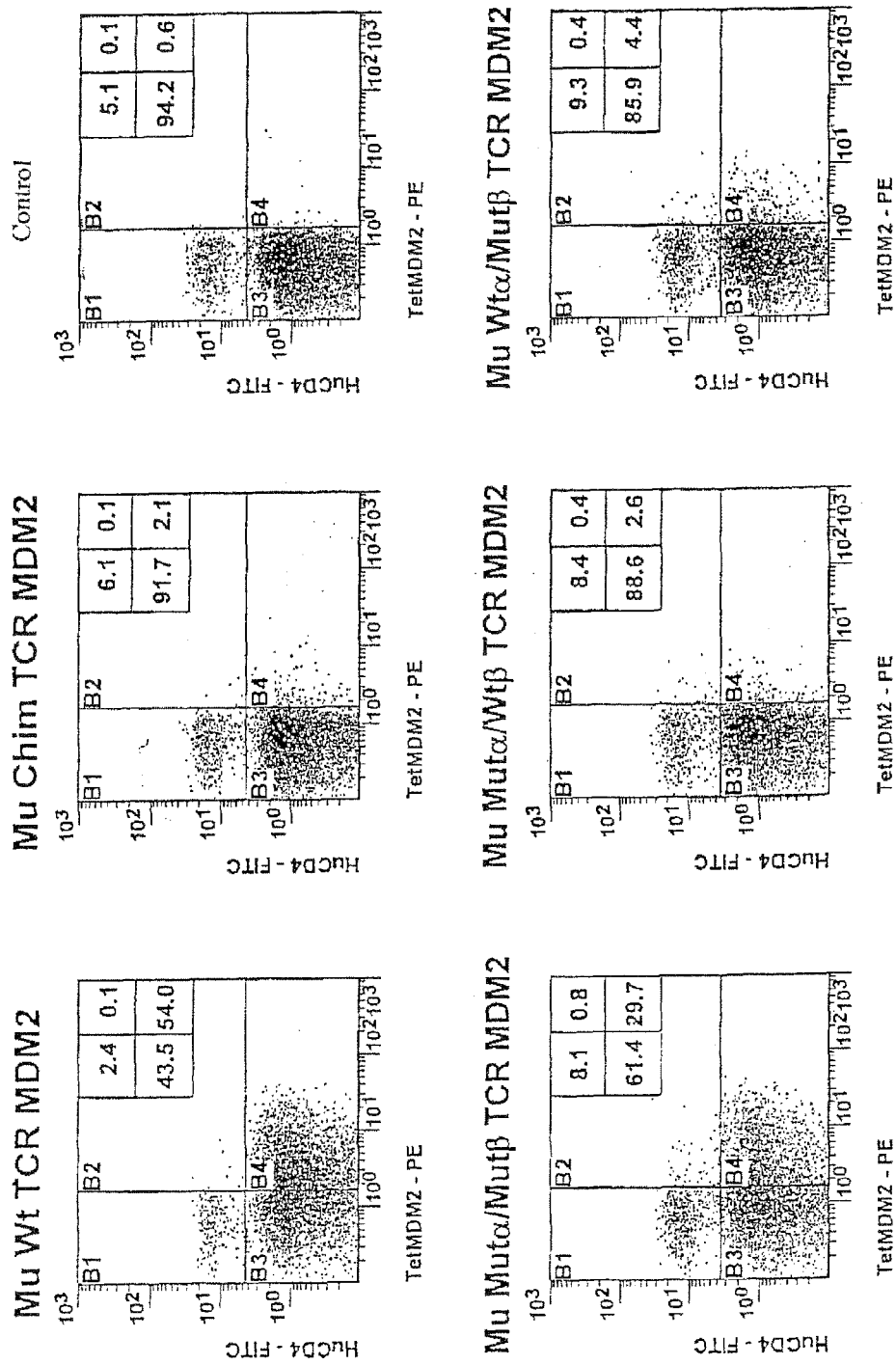

FIG. 8 shows the FACS-analysis of human transduced T-cells that each was provided with the different combinations of the TCR-constructs as described in FIG. 3. Depicted is a 2-fold staining of TetMDM2-PE and CD4-FITC: the tetramer-staining enables the determination of functional, heterodimeric αβ3TCR, thus the indirect determination of the α-chain. Only CD8-positive T-cells can be stained since the tetramer in case of moderately to highly affine binding TCR is binding dependent from CD8.

Figure 9:
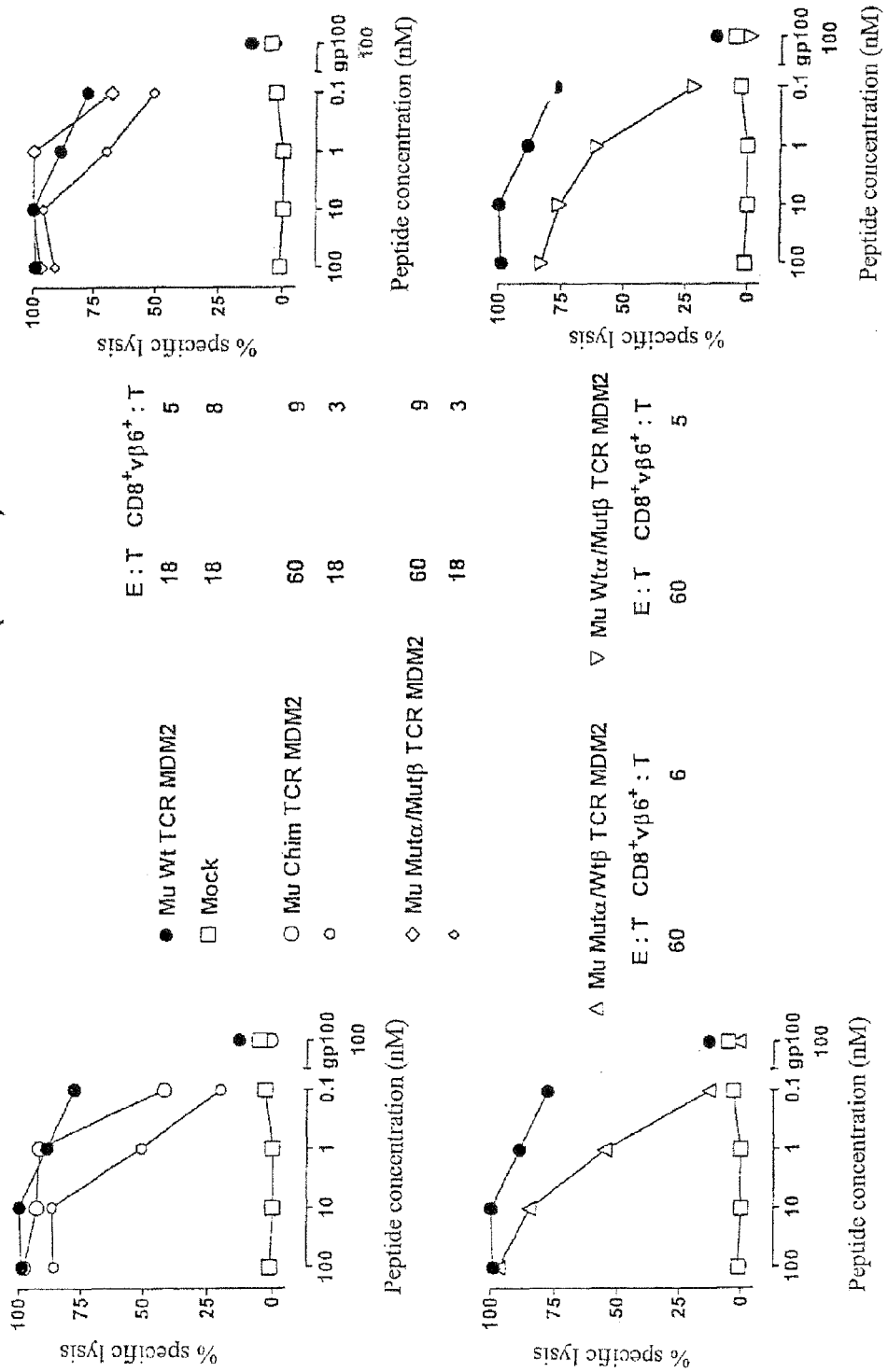

FIG. 9 shows the cytotoxicity-assay (Stanislawski & Voss et al, 2001) with the combined double-chain TCR shown in FIG. 3: TAP-deficient T2 were loaded exogenously with the indicated MDM2(81-88)-peptide-concentrations and tested for recognition by the transduced T-cells: the extent of lysis is reflected in the quantity by the $^{51}Cr$ that was taken up into the cells and released by lysis. A gp100-derived peptide functioned as a relevant peptide. The "effector: target"-Ratio as well as the corrected $CD8^+vβ6^+$-ratio are given since these varied between the different transduction-approaches.

Figure 10:
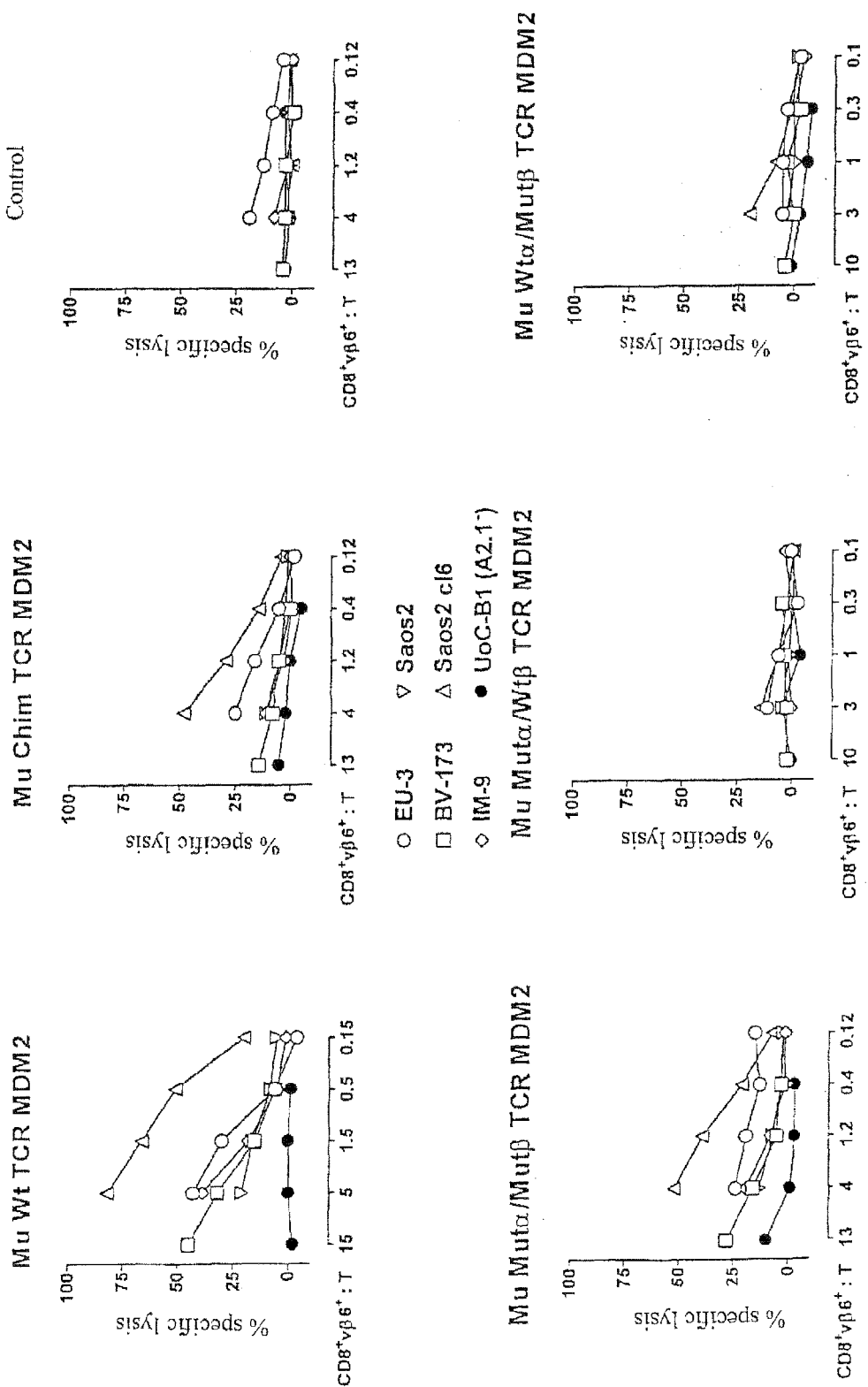

FIG. 10 shows the cytotoxicity-assay (Stanislawski & Voss et al, 2001) with the combined double-chains TCR shown in FIG. 3: HLA-A2-positive leukemia-cell lines of different origin (ATCC (American Type Culture Collection, Manassas, USA), DSMZ (Deutsche Sammlung von Mikroorganismen and Zellkulturen GmbH, Braunschweig)), that over expressed MDM2 and process the MDM2(81-88)-peptide were used as "target". The A2-negative leukemia-cell line UocB1 and the MDM2-negative cell line Saos2 served as negative control. A MDM2-transfectant of Saos2, Saos2 c16, was also specifically recognized.

FIG. 11 shows the different possibilities of the inversion of steric relations, the charges or both, according to the method according to the invention.

EXAMPLES

Point mutants (Mut) of the murine wild type-TCR (Wt) were to be determined that fulfill the above described "knob-hole"-model: a pairing of chains should occur only in those TCR-chains that carry each one of the sterically inverted amino acid partners, whereas the combination of wild type and mutated chain in both conceivable orientations should be affected (FIG. 3). In addition, the combined TCR had to be tested after introduction into human T-cells in view of their structural avidity, i.e. their structural integrity and in view of their functional avidity, i.e. the maintenance of the peptide-dependent effector function (Bullock et al., 2001). The MDM2(81-88)-specific T-cell-receptors as described above and identified in our laboratory whose amino acid sequence of the constant domains is nearly identical to the murine TCR 1.pdb for which structural data is present (FIG. 4a/b, Garcia et al., 1998) and that exhibits a high homology in the variable domains to this, was used as a model system. MDM2 is a human regulatory proto-oncoprotein that counter regulates the expression of the tumor suppressor protein p53 (Stanislawski & Voss et al., 2001).

The fashion of the selection of the point mutations occurred after the analysis of published TCR-crystal structures and the comparison of homology of murine and human sequences. The point mutations were then introduced into the murine TCRs being similar to the human, and experimentally functionally tested. It can be derived from the homology comparison against human sequences that the structural situations in human TCRs in the intermediate surroundings of the amino acid exchanges are nearly identical and therefore a pairing of "mutated murine chain with human wild type-chain" in the configuration "αTCR-βTCR" or "βTCR-αTCR" must be likewise reduced.

The point mutants so far are not yet absolutely functional, nevertheless interfere noticeably with the formation of unwanted pairs. These amino acid exchanges follow the general "knob-hole"-model which indicates to invert the proportions of interacting amino acids in order to introduce a chain-specific interaction. Further mutations can be provided in the chains as already generated in order to further increase the specificity. This aspect is also included in the scope of the present invention.

The selection of point mutants was made in such a manner that these, at least for different murine TCR of different peptide-specificity could be generalized. In addition, these point mutants can also be applied to human TCRs since the murine TCR in a parallel project, by maintaining the peptide-effector-function, should be maximally humanized in order to avoid immune reactions against the exogenic TCR. Therefore, preferentially identical amino acids versus homologous amino acids should be selected. A sequence comparison of several murine and human TCR-sequences showed an exceedingly high homology in the constant domain, whereas the variable domain exhibited only low homologies (FIG. 4a/b). There are numerous amino acids that are conserved in the contact area of the heterodimeric chains between human and mouse, and had to be individually verified for the solution of the problem (FIG. 2). As an essential criterion, the amino acids as selected, must be integrateable into the "knob hole"-model, i.e. an amino acid having a correspondingly large side chain must interfere with a smaller amino acid of the other chain. Therefore, it was a priori irrelevant in which of both chains the large amino acid was present. As large amino acids, tryptophane, lysine, arginine, phenylalanine and tyrosine could be taken into account, as small, in particular, glycine, serine, and alanine. The directly adjacent amino acids should, in case of the potential inversion of the steric situations at the respective position, should behave as inert as possible, i.e. should not have a pronounced interaction whether hydrophobic or charged nature with the interacting pair of amino acids.

For the examination of murine TCR-structures the coordinative data of the murine TCR 1.pdb (Garcia et al., 1998) was downloaded from the "Brookhaven Protein Database" (www.resb.org/pdb) charged and visualized by means of the structure-depicting software "Swiss-PDBViewer" (www.expasy.ch/spclbv).

The following position was found to be particularly attractive: arginine$^{195}$ of the βTCR from 1.pdb, in a nearly stretched all-trans-conformation of a side chain, pointed in the direction of the αTCR (FIG. 5). Compared to the guanidinium-Group of Arg$^{195}$ Gly$^{179}$ of the αTCR is present in an ideal Van der Waals-distance. The amino acid sequence on the side of the α-chain around Gly$^{179}$ is

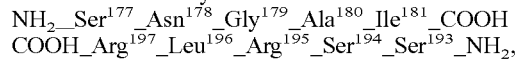

COOH_Arg$^{197}$_Leu$^{196}$_Arg$^{195}$_Ser$^{194}$_Ser$^{193}$_NH$_2$.

The opposing β-strand of the β-chain that contains the Arg$^{195}$ is anti-parallel and approximately twisted by 30° to the β-strand of the α-chains: through this the side chains of the neighboring β-strands come into the sterical vicinity to the interacting pair of amino acids. The β-chains-amino acid sequence at this position is identical between human and mouse, the one of α-chain is largely homologous: Gly$^{179}$ is replaced by the likewise small amino acid serine in human, Ile$^{181}$ by the homologous valine. The sequences of the β-strands of both chains that are neighboring on the same level to the Gly$^{179}$/Arg$^{195}$ are identical over a length of 5 amino acids between human and mouse and are therefore also the potential interacting partner immediately around Gly$^{179}$/Arg$^{195}$ (FIG. 4a/b).

At best, weak hydrophobic interactions of neighboring side chains must be considered for the pair of amino acids. The contact areas of chains at this position is not densely packed: only few long chain amino acids point into the direction of the opposing chain or offer extensive hydrophobic Van der Waals-contacts. This again stresses the structural meaning of the projecting side chain of the Arg$^{195}$. The pair of amino acids is intermediately localized in a drilled β-sheet of the constant domain being partially wound around itself of both chains (FIG. 6a/b): each β-sheet consists of four β-strands out of which an intermediate β-strand contains one of the targeted amino acids, respectively. Each β-sheet of the individual chain for itself forms numerous H-bridges but none of them via their amino acid side chains towards the opposing chain. Exclusively Arg$^{195}$ by the terminal nitrogen of the guanidinium-group forms two H-bridges towards the opposing main chain oxygen and side chain oxygen of Thr$^{166}$ of the α-chain. A central bridge is formed in a contact region that is apart from that characterized by few salt bridges and dipole-dipole interchanging effects as well as by a low packing of hydrophobic amino acids. At the edge of the cavity to be formed (FIG. 6a) there are numerous contacts between the chains, nevertheless those are not comparably well positioned in the middle of the contact area of the respective wound β-sheets. The stretched conformation of the Arg$^{195}$ as well as the low hydrophobic packing enable an inversion of the amino acids without essentially affecting the local structure. A mutated Arg$^{179}$ of the αTCR would likewise be able to at least form an H-bridge towards the main chain oxygen of Ser$^{173}$ of the opposing β-strand of the βTCR without that the mutated Gly$^{195}$ would provide any interference (FIG. 6b). A slight positive charge shift of the guanidinium-group from the α-chain in the direction of the β-chain results. The amino acids do not have to be qualitatively modified in order to generate comparable steric (i.e. ideal hydrophobic distances) and polar relations (i.e. H-bridges). The positions in MDM2 (81-88)-specific TCR that are identical to Arg$^{195}$ and Gly$^{179}$ of 1.pdb are Arg$^{208}$ and Gly$^{192}$. In human T-cell-receptors the arginine of the β-chain is conserved, whereas the likewise small amino acid serine is present at the position of the glycine of the α-chain (1bd2; FIG. 4). A publication about mutated or truncated TCR proves the importance of the constant domain for the pairing of chains by Coulomb-forces between charged amino acids residues of the region Ser$^{188}$-Leu$^{213}$ of the β-chain wherein the point mutant is positioned that is described by the inventors (Li et al., 1996).

The corresponding mutation are introduced in the respective MDM2(81-88)-specific TCR-genes that were already individually present in the retroviral vector pBullet (Willemsen et al., 2000) with the aid of the "Quikchange™ Site-Directed Mutagenesis"-Kit (Stratagene) (Stanislawski & Voss et al., 2001).

The adoptive transfer into human T-cells occurred principally as described in Stanislawski & Voss et al (2001). The co-transfection system (Weijtens et al., 1998) that provides a co-transfection of individual plasmids with each of a chain of the heterodimeric TCR encoded as transgene, enables the combination of all conceivable wild type and mutated TCR-chains. The wild type TCR versus the TCR being mutated in both chains versus a TCR being mutated in only one chain should be analyzed structurally by FACS-analysis and functionally by cytotoxic lysis of antigen-presenting cells (APC) as lyseable target cells. Therefore, in the Following designated "hybrid TCR" being mutated in only one chain serves as a model for the "unwanted" TCR-pair of chains from mutated exogenic murine α- or β-chain and the wild type endogenic human β- or α-chain (FIG. 3), as could be hypothetically present in case of an adoptive transfer in human T-cells. This could be assumed since the structural backbone as well as the amino acid sequences of human and murine TCR in the constant domain are strongly conserved and can potentially interact and mutations will exhibit a comparable effect on pairing of chains and antigen recognition. Hereby, the endogenic TCR being present in the human T-cells did not interfere with the analysis of different murine TCR-combinations since the mutations of the murine chains could at best have a parallel effect on the pairing of chains to the human "pendant". In addition, it is important to perform these experiments in an experimental design that is as similar as possible to the clinical application.

In order to start with the assumption that all T-cells contain the transgene, after transduction the T-cells were selected by G418 (selection marker for the β-chain that is following the transgene via an IRES-element) as well as via puromycin (selection marker for the α-chain). Thus, only those T-cells survive that produce the bicistronic mRNA from βTCR-transgene and G418-marker as well as the bicisronic mRNA from αTCR and puromycin. Differences in the FACS-staining therefore do not result from differences in transduction efficiency from the human T-cells but are reflecting the respective TCR-stability.

The structural avidity as an expression of stable expression of the wild type as well as the mutated TCR was analyzed on the one hand via the sub-family of the specific staining of β-chain (vbeta6-FITC; FIG. 7) as well as the TCR-specificity distinguishing staining by means of MDM2(81-88)-specific TCR-tetramers (Klenerman et al., 2002, FIG. 8) by means of FACS-analysis. The tetramers were produced in the laboratory of Dr. Pedro Romero (University Lausanne, Switzerland), and provided for scientific purposes.

It could already be seen from the vβ6-staining that the "hybrid" TCRs, Mu Mutα/Wtβ TCR MDM2 and Mu Wtβ/Mutα TCR MDM2, did express the β-chain at least as unstable as was known from a partially humanized TCR, Mu Chim TCR MDM2 (FIG. 7). A further indicator of a prominent TCR-instability was the tetramer-colorability, which was nearly missing (FIG. 8). The TCRs that were mutated in both chains, Mu Mutα/Mutβ TCR MDM2, were determined in the vβ6—as well as the tetramer-staining in a nearly comparable fashion to the murine wild type-chains, Mu Wt TCR MDM2.

The efficiency of lysis as a measure of the functional avidity was measured in the chrome-release assay or cytotoxicity assay. For this, the cell line T2, that is unable to load endogenically processed peptides onto MHC-molecules and to transport the complexes to the cellular surface, was exogenically loaded with the MDM2(81-88)-peptide in a concentration dependent manner, and the half maximal lysis as a measure of the recognition was measured in a peptide titration (FIG. 9). The different vβ6—as well as CD8-positivity of the differently transduced T-cell-populations were indicated by stating the $CD8^+v\beta6^+$:T-ratios in addition to the common E:T (effector:target)-ratios: differences in the efficiency of lysis therefore reflect the differently combined TCR-constructs through correcting both T-cell-phenotype-markers as an expression of the percent strength of expression of the βTCR ($v\beta6^+$) and the percent strength of the cytotoxic T-cell-population ($CD8^+$). Congruent with the data of the structural avidity it could be taken from the functional data that the "hybrid" TCRs were markedly affected in the efficiency of lysis compared to the wild type, and still were worse than the chimeric partially humanized TCR, although in these a complete domain (Cα or Cβ, respectively) and not only one amino acid was exchanged like in the "hybrid" TCRs. The TCR being mutated in both chains mutated TCR, Mutα/Mutβ TCR MDM2, exhibited only slightly worsened efficiencies of lysis compared to the wild type.

These quantitative differences then should be examined whether there is a critical half maximal lyses, i.e. a threshold at which target cells that endogenically present the respective peptide, are first recognized. For this, different target cells were examined in a cytotoxicity assay (FIG. 10): here, Saos2 serves as a negative control of the MDM2-expression, whereas Saos2 c16 represents a MDM2-transfectant with positive MDM2(81-88)-processing. The leukemia-cell line UocB1 is HLA-A2-negative and indicates the MHC-restriction of the transduced T-cells. The other leukemia-cell lines EU-3, BV-173 and IM-9 are of different origin (ATCC, DSMZ) and prove the generalization of the MDM2(81-88)-recognition by the transduced human T-cells. Also in this case it could be shown that the TCR being mutated in both chains is comparable to the wild type and better than the chimeric TCR in recognizing the endogenic "targets". Although the "hybrid" TCR half maximally lyses the exogenically loaded cell line T2 up to 1 nM peptide (FIG. 9), these to not recognize the malign cell lines: obviously, the peptide presentation of MDM2(81-88) has dropped below a critical value, below which this is no longer recognized. Saos2 c16 is weakly recognized, which most likely can be explained with the heterologous, promoter-driven strong expression of MDM2.

The data of the structural and functional avidity therefore are congruent and prove the effectiveness of the selected point mutants in a murine TCR-model in human T-cells in order to drastically impair unwanted "pairing" of heterodimeric "hybrid" αβTCR.

Transduction of Human Peripheral Blood Lymphocytes (PBLs)

For the transduction of human peripheric blood T-lymphocytes, a functional derivative of the pStitch-system (Weijtens et al., 1999) was used. The retroviral genes required for packaging were encoded by individual plasmids by way of a co-transfection of the packaging cell line 293T (Soneoka et al., 1995): pHit60 encodes for the gag-pol—structure—and polymerase-gene from the Moloney murine leukemia virus (MoMuLV), pColt-Galv for the env—envelope protein of the "gibbon ape leukemia virus", that is able to bind to the $Na^+$-/phosphate-synporter pit of human cells, and thereby to transduce the latter. The chimeric viral particles therefore exhibit an amphotrophic pseudotype, and are able to transduce different mammalian cells, apart from mouse.

Transfection of the Packaging Cell Line 293T

The isolated bacterial clone of the T-cell-receptor-genes cloned in the pStitch-derivative were purified by means of plasmid-preparations, that assures a removal of residual endotoxines (Qiagen, product 12362), and adjusted to 1 μg/μl. The DNA was transiently introduced into the packaging cell line 293T (GiboBRL-Life Technologies, product 18306-019) via the calcium phosphate-precipitation. Here, in the context of the modified T-cell-receptors, αTCR and βTCR up to 80 μg DNA are employed:

20 μg αTCR-construct
20 μg TCR-construct
20 μg pColt-Galv
20 μg pHit 60

In case of single chain-TCRs 60 μg DNA are used. 293T were grown in a modified DMEM-medium (DMEM/H):

DMEM, 4.5% glucose (BioWhittaker)
10% heat inactivated FKS
2 mM glutamine
1× penicillin/streptomycin
1× non-essential amino acids
25 mM HEPES On the day before the transfection, the 293T cells were seeded at $0.9*10^6$ cells per T25-flask and transfection approach in 5 ml DMEM/H. 4 h before transfection the medium was replaced with fresh DMEM-H (3 ml) that was warmed to room temperature (RT). The transfection occurred according to the instruction of the commercial protocol (Invitrogen). 1 ml of the transfection approach was pipetted into the respective flask by careful drop wise addition. The DNA-$Ca_3(PO_4)_2$-precipitate should spread out finely distributed onto the adherent cells.

On the following morning, the medium was replaced with fresh DMEM/H which was warmed to room temperature. 6 h later, the co-cultivation with the activated PBLs took place.

Transduction of the Activated PBLs—Activation of Peripheric Blood Lymphocytes (PBLs)

3 days before the scheduled co-cultivation ficoll-treated PBLs were seeded at $2*10^6$ cells/ml in huRPMI-P in each 2 ml of a 24 well-plate (cellular tissue-treated surfaces). The activation occurred via the cross-linking antibody OKT-3 (Orthoclone-Diagnostics) at 20 ng/ml.

huRPMI-P:

RPMI 1640 (2 mM glutamine) without phosphate (Life Tee., 11877-032)

10% human, heat inactivated AB-serum (HLA-A2.1 seropositive)

25 mMHEPES

1× penicillin/streptomycin (Life Tec.)

The plates were incubated in an incubator at 37° C. and 5% $CO_2$.

Co-Cultivation

For co-cultivation, the activated PBLs from the respective wells of a 24-well-plate were pooled and counted. Adherent monocytes were discarded. The cells were centrifuged (1500 rpm, 5 min, RT) and resuspended in a concentration of $2.5*10^6$ cells/ml in fresh huRPMI-P, and put back into the incubator. Prior to this, the medium was adjusted to 400 U/ml IL-2 (Chiron) and 5 µg/ml polybren (Sigma).

Each transfection approach was consecutively trypsinated 6 h after the change of medium: for this, each T25 was washed with 3 ml HBSS (Life Technologies), incubated with 1 ml trypsin-EDTA (Life Technologies) for maximal 5 minutes, the dissolved cells were quantitatively taken up, and added dropwise while stirring to 4 ml prepared huRPMI-P (RT). The 293T cells were irradiated with 2500 rad. They were centrifuged (1500 rpm, 5 min, RT) and resuspended in 4 ml fresh, adjusted huRPMI-P, supplemented with 400 U/ml IL-2 and 5 µg/ml polybren. 1 ml of the adjusted PBLs were added to the preparation, and the preparation ($0.5*10^6$ PBLs/ml) was incubated for three days in an incubator (37° C., 5% $CO_2$).

On day 3 following co-cultivation, the suspended PBLs were taken up and resuspended in fresh medium huRPMI-P, supplemented with 40 U/ml IL-2 (Chiron) and 2.5 µl CD3/CD28-beads, at $1*10^6$ cells/ml. 3 days later, an anew split in fresh medium took place. Within these 7 days, it was maximally expanded to the transition on T75-flasks. These cells could be directly employed in an immunological staining (FACS-analysis) or in a classical $^{51}$chromium release assay.

Examples of the FACS-Analysis

Following the retroviral transduction, the above described constructs were analyzed in "fluorescence activated cell sorting" (FACS). For this, $0.25*10^6$ cells were saturating stained with fluorophor-labelled antibodies: the heterologous expressed mutated β-chain was detected with anti-vβ-FITC (BD); the total of the T-cells by the marker anti-CD3-PC5 (Coulter-Beckman). A sample that was transduced with the empty pStitch-derivative served as a negative-control. The expression could be reproduced in several donors of HLA-A2-positive T-cells. For the tetramer-staining, 5 µl of a 0.28 mg/ml stock solution for 45 min at 8° C. were used.

Cytolytic Activity of the Transduced T-Cells

The transduced T-cells were analyzed for their cytotoxic specificity in a classical $^{51}$chromium-release assay. In this system target cells were radioactively labeled by the incorporation of $^{51}$chromium. If the retrovirally modified effector cells peptide-specifically recognized the target cell, the latter was driven into apoptosis by the effector functions of the T-cell, and killed by lysis. The extent of the released chromium-nuclide allows for a conclusion about the effectiveness of the cellular recognition and lysis. The affectivity was tested over a broad range of the ratio of tested effector cells to target cells (E:T) that were used. A murine MDM2-81-88 peptide specific T-cell-clone served as a reference, from which the T-cell receptor gene was isolated. Target cells were:

T2: human TAP-deficient cell line, which was to be loaded exogenously with any peptide. The specifically mutated peptide was MDM2-81-88, an irrelevant control-peptide was derived from the influenza-matrix protein FluM1.

Saos-2/6: transfectant of the human osteosarcoma Saos-2-cell line that heterologously expresses and endogenously processes MDM2.

UocB11, EU-3: pre-B-cell-leukemia

IM-9: plasmocytoma

BV173: pre-B-cell-leukemia

U30031PCT

Johannes Gutenberg-Universitat Mainz

---

We claim:

1. An in vitro method for producing a heterodimeric specific wild type- or chimeric T-cell receptor (TCR), said TCR being a human TCR, a murine TCR or a humanized murine TCR, the method comprising:

(a) providing DNA-molecules in joint or separate mutagenesis vector system(s), the DNA-molecules comprising the coding regions for a first and second chain of a TCR, said first and second chain of said TCR interacting at at least one surface in the constant regions of the first and second chains, (b) mutagenizing the DNA-molecules to produce individual mutated DNA-molecules, wherein the nucleic acid sequence encoding the first chain is mutagenized to encode the first chain comprising a substitution in an amino acid in the at least one surface within the constant region of the first chain, wherein the amino acid interacts with the second chain and the amino acid introduced after mutagenesis in the at least one surface of the first chain provides a sterically projecting group in the constant domain of the first chain and the nucleic acid sequence encoding the second chain is mutagenized to encode the second chain comprising a substitution in an amino acid in the at least one surface within the constant region that of the second chain, wherein the amino acid interacts with the first chain and the amino acid introduced after mutagenesis in the at least one surface of the second chain provides a sterically recessed group in the constant domain of the second chain, (c) translating the mutated DNA molecules from step (b), such that pairing of the heterodimeric specific first-chain/second-chain TCR being mutated at the at least one surface within the constant region is selectively promoted, and (d) expressing in vitro the heterodimeric first-chain/second-chain TCR by a T-cell, wherein the first chain and second chain of said TCR interact via the sterically projecting group and the sterically recessed group at said at least one surface located in the constant regions of said first and second chains wherein an amino acid that has been introduced after the mutagenesis of the DNA-molecules that introduces a sterically recessing group compared to the initial sequence is selected from glycine, serine, threonine, valine and alanine, and wherein an amino acid that has been introduced after the mutagenesis of the DNA-molecules that introduces a sterically projecting group compared to the initial sequence is selected from tryptophan, lysine, arginine, phenylalanine, cysteine and tyrosine.

2. The method according to claim 1, wherein step c) is replaced by the following steps:
   (c') optionally, sub-cloning of the mutated DNA molecules into a suitable transfection-vector system,
   (c") transfection or co-transfection or transduction of at least two of the mutated DNA molecules into a mutant TCR-deficient T-cell, and
   (c''') expression of the heterodimeric first-chain/second-chain TCR in a recombinant T-cell.

3. The method according to claim 1, wherein step c) is replaced by the following steps:
   c') In vitro-translation or in vivo-translation of at least two of the individual mutated DNA molecules from step (b) and, optionally, subsequent isolation or purification or both isolation and purification of the translated first and second chains, such that the pairing of the heterodimeric specific first-chain/second-chain TCR being mutated at least on one surface is selectively promoted, and
   c") introduction of the mutated specific first-chain/second-chain TCR into a T-cell.

4. method according to claim 3, wherein the in vivo translation takes place in a host cell.

5. The method according to claim 3, wherein the introduction takes place by liposome-transfer.

6. The method according to claim 1, wherein the TCR is an alpha/beta TCR, gamma/delta TCR or a partially humanized TCR.

7. The method according to claim 1, wherein the amino acids as introduced after the mutagenesis of the DNA-molecules are further suitably chemically modified, in order to thereby introduce a sterically projecting group or a sterically recessing group.

8. The method according to claim 1, wherein the amino acids as introduced after the mutagenesis of the DNA-molecules directly provide the sterically projecting group or the sterically recessing group.

9. The method according to claim 1, wherein the amino acids as introduced by the mutagenesis of the DNA-molecules are chosen in such a manner that a mutual exchange of the amino acids on the surfaces of the interacting chains of the TCR is achieved.

10. The method according to claim 1, wherein at least two surfaces of a TCR-chain are simultaneously subjected to mutagenesis.

11. The method according to claim 1, wherein the mutagenesis of the TCR-chains also leads to humanization of the TCR.

12. The method according to claim 1, wherein the alpha- and beta-chains of a mouse-double-minute-2 (MDM2)(81-88)-specific TCR are used as alpha-chain and beta-chain, and wherein the $Gly_{192}$ of the constant region of the alpha-chain and the $Arg_{208}$ of the constant region of the beta-chain are exchanged by $Arg_{192}$ in the constant region of the alpha-chain and by $Gly_{208}$ in the constant region of the beta-chain.

13. The method according to claim 12, wherein simultaneously with or subsequent to the exchanges at positions 192 and 208, additional positions are modified in the chains.

14. The method according to claim 1, wherein a retroviral vector is used as a transfection system.

15. The method according to claim 1, wherein said TCR is a murine TCR.

16. The method according to claim 1, wherein said TCR is a human TCR.

* * * * *

UNITED STATES PATENT AND TRADEMARK OFFICE
CERTIFICATE OF CORRECTION

PATENT NO. : 9,062,127 B2
APPLICATION NO. : 12/952259
DATED : June 23, 2015
INVENTOR(S) : Ralf-Holger Voss and Theobald Matthias It is certified that error appears in the above-identified patent and that said Letters Patent is hereby corrected as shown below:

In the Specification:

Column 5,
Line 59, "that is is by" should read --that is, by--.

Column 11,
Line 35, "4-region" should read --ζ-region--.

Column 14,
Line 67, "poi for" should read --*pol* for--.

Column 16,
Line 58, "I-cells," should read --T-cells,--.

Column 17,
Lines 7-8, "and/or prophylactics prophylactics, in" should read --and/or prophylactics, in--.

Column 19,
Line 50, "αβ3TCR," should read --αβTCR,--.

Column 21,
Line 30, "_NH₂," should read --_NH₂.--.

Column 22,
Line 7, "3TCR" should read --βTCR--.

Column 23,
Line 21, "vβ6—as" should read --vβ6- as--.
Line 32, "vβ6—as" should read --vβ6- as--.

Signed and Sealed this
Second Day of August, 2016

Michelle K. Lee
*Director of the United States Patent and Trademark Office*

Column 25,
Line 3, "Tee.," should read --Tec.,--.

In the Claims:

Column 35,
Line 36, "method" should read --The method--.